United States Patent
Alferness et al.

(10) Patent No.: US 6,564,094 B2
(45) Date of Patent: May 13, 2003

(54) CARDIAC DISEASE TREATMENT AND DEVICE

(75) Inventors: Clif Alferness, Redmond, WA (US); J. Edward Shapland, Vadnais Heights, MN (US); Michael Girard, Lino Lakes, MN (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 336 days.

(21) Appl. No.: 09/747,453

(22) Filed: Dec. 22, 2000

(65) Prior Publication Data

US 2002/0082647 A1 Jun. 27, 2002

(51) Int. Cl.⁷ .............................. A61N 1/362
(52) U.S. Cl. ........................ 607/9; 607/129
(58) Field of Search .................. 607/4, 5, 9, 116, 607/119, 120, 129; 600/16, 37; 424/422, 423, 426; 623/3.1, 3.11

(56) References Cited

U.S. PATENT DOCUMENTS

| | | | |
|---|---|---|---|
| 3,983,863 A | 10/1976 | Janke et al. ............ 600/37 |
| 4,048,990 A | 9/1977 | Goetz ................... 601/153 |
| 4,428,375 A | 1/1984 | Ellman ................... 600/151 |
| 4,630,597 A | 12/1986 | Kantrowitz et al. ...... 600/18 |
| 4,690,134 A | 9/1987 | Snyders .................. 601/153 |
| 4,765,341 A * | 8/1988 | Mower et al. ............ 607/116 |
| 4,821,723 A | 4/1989 | Baker, Jr. et al. ......... 607/7 |
| 4,878,890 A | 11/1989 | Bilweis ................. 600/37 |
| 4,913,903 A * | 4/1990 | Sudmann et al. ......... 424/426 |
| 4,936,857 A | 6/1990 | Kulik .................... 623/3.1 |
| 4,957,477 A | 9/1990 | Lundbäck ................ 600/16 |
| 4,973,300 A | 11/1990 | Wright .................. 600/37 |
| 4,976,730 A | 12/1990 | Kwan-Gett .............. 623/3.26 |
| 5,057,117 A | 10/1991 | Atweh .................. 606/151 |
| 5,087,243 A | 2/1992 | Avitall .................. 604/20 |
| 5,131,905 A | 7/1992 | Grooters ................ 600/16 |
| 5,150,706 A | 9/1992 | Cox et al. ............... 607/105 |

(List continued on next page.)

FOREIGN PATENT DOCUMENTS

| | | |
|---|---|---|
| DE | 295 17 393 U 1 | 3/1996 |
| EP | 0 280 564 A2 | 8/1988 |
| JP | 60-203250 | 10/1985 |
| JP | 01-145066 | 6/1989 |
| SU | 1009457 A | 4/1983 |
| WO | WO 98/29041 | 7/1998 |
| WO | WO 98/58598 | 12/1998 |
| WO | WO 99/44534 | 9/1999 |
| WO | WO 00/06026 | 2/2000 |
| WO | WO 00/06027 | 2/2000 |
| WO | WO 00/06028 | 2/2000 |
| WO | WO 00/16700 | 3/2000 |

OTHER PUBLICATIONS

Capomolla, S. et al., "Dobutamine and nitroprusside infusion in patients with severe congestive heart failure: Hemodynamic improvement by discordant effects on mitral regurgitation, left atrial function, and ventricular function",

*Primary Examiner*—Willis R. Wolfe (List continued on next page.)

(74) *Attorney, Agent, or Firm*—Merchant & Gould P.C.

(57) ABSTRACT

A device for treating cardiac disease is provided. The device includes biologically compatible material, an electrotherapy instrument, and a placement apparatus capable of capable of releasably securing a lead of the electrotherapy instrument to the biologically compatible material. In one embodiment, the biologically compatible material is a patch that is configured to be secured to the epicardial surface of the heart. In an alternate embodiment, the biologically compatible material is constructed as a jacket of flexible material designed to be secured to the heart. Examples of electrotherapy instruments include a cardiac pacing device and a defibrillating device.

41 Claims, 12 Drawing Sheets

U.S. PATENT DOCUMENTS

| | | | |
|---|---|---|---|
| 5,154,182 A | * 10/1992 | Moaddeb | 607/120 |
| 5,186,711 A | 2/1993 | Epstein | 600/37 |
| 5,192,314 A | 3/1993 | Daskalakis | 623/3.21 |
| 5,256,132 A | 10/1993 | Snyders | 600/16 |
| 5,290,217 A | 3/1994 | Campos | 600/37 |
| 5,356,432 A | 10/1994 | Rutkow et al. | 623/23.72 |
| 5,383,840 A | 1/1995 | Heilman et al. | 600/17 |
| 5,385,156 A | 1/1995 | Oliva | 128/898 |
| 5,429,584 A | 7/1995 | Chiu | 600/18 |
| 5,507,779 A | 4/1996 | Altman | 607/5 |
| 5,524,633 A | 6/1996 | Heaven et al. | 600/562 |
| 5,527,358 A | * 6/1996 | Mehmanesh et al. | 607/129 |
| 5,603,337 A | 2/1997 | Jarvik | 128/898 |
| 5,647,380 A | 7/1997 | Campbell et al. | 128/898 |
| 5,702,343 A | 12/1997 | Alferness | 600/37 |
| 5,713,954 A | 2/1998 | Rosenberg et al. | 600/17 |
| 5,800,528 A | 9/1998 | Lederman et al. | 600/37 |
| 5,849,033 A | * 12/1998 | Mehmanesh et al. | 607/129 |
| 5,961,440 A | 10/1999 | Schweich, Jr. et al. | 600/16 |
| 5,990,378 A | 11/1999 | Ellis | 623/11.11 |
| 6,045,497 A | 4/2000 | Schweich, Jr. et al. | 600/16 |
| 6,050,936 A | 4/2000 | Schweich, Jr. et al. | 600/37 |
| 6,059,715 A | 5/2000 | Schweich, Jr. et al. | 600/16 |
| 6,330,481 B1 | * 12/2001 | Van Wijk et al. | 607/129 |
| 6,385,491 B1 | * 5/2002 | Lindemans et al. | 607/120 |
| 6,432,039 B1 | * 8/2002 | Wardle | 600/37 *American Heart Journal*, vol. 134, pp. 1089–1098 (Dec. 1997). |

OTHER PUBLICATIONS

Capouya, E. et al., "Girdling Effect of Nonstimulated Cardiomyoplasty on Left Ventricular Function", *Ann Thorac. Surg.*, vol. 56, pp. 867–871 (1993).

Cohn, J., "The Management of Chronic Heart Failure", *The New England Journal of Medicine*, vol. 335, No. 7, pp. 490–498 (Aug. 15, 1996).

Coletta, C. et al., "Prognostic value of left ventricular volume response during dobutamine stress echocardiography", *European Heart Journal*, vol. 18, pp. 1599–1605 (Oct. 1997).

Guasp, F., "Una prótesis contentiva para el tratamiento de la miocardiopatia dilatada", *Revista Española de Cardiologia*, vol. 51, No. 7, pp. 521–528 (Jul. 1998).

Kass, D. et al., "Reverse Remodeling From Cardiomyoplasty in Human Heart Failure External Constraint Versus Active Assist", *Circulation*, vol. 91, No. 9, pp. 2314–2318 (May 1, 1995).

Levin, H. et al., "Reversal of Chronic Ventricular Dilation in Patients With End–Stage Cardiomyopathy by Prolonged Mechanical Unloading", *Circulation*, vol. 91, No. 11, pp. 2717–2720 (Jun. 1, 1995).

Oh, J. et al., "The Effects Of Prosthetic Cardiac Binding and Adynamic Cardiomyoplasty In A Model Of Dilated Cardiomyopathy", *The Journal of Thoracic and Cardiovascular Surgery*, vol. 116, No. 1, pp. 148–153 (Jul. 1998).

Paling, D., "Warp Knitting Technology", *Columbine Press*, p. 111 (1965).

Vaynblat, M. et al., "Cardiac Binding in Experimental Heart Failure", *Ann. Thorac. Surg.*, vol. 64, 11 pages (1997).

* cited by examiner

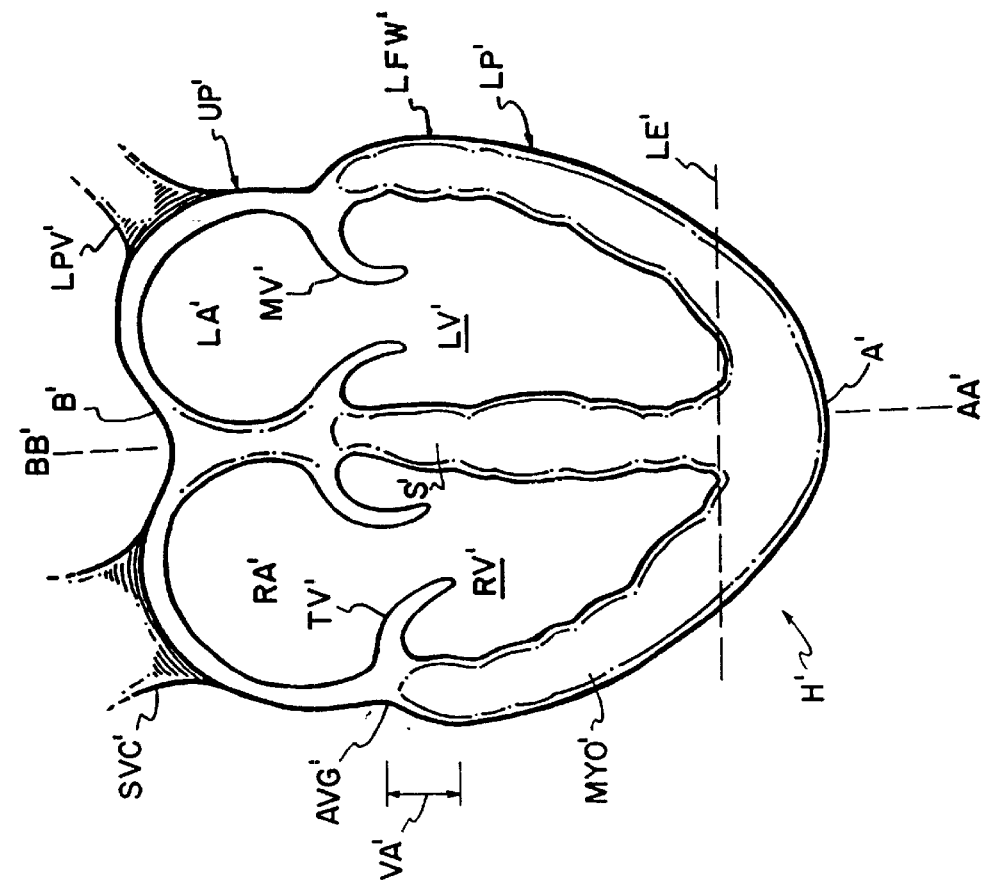
FIG. IA
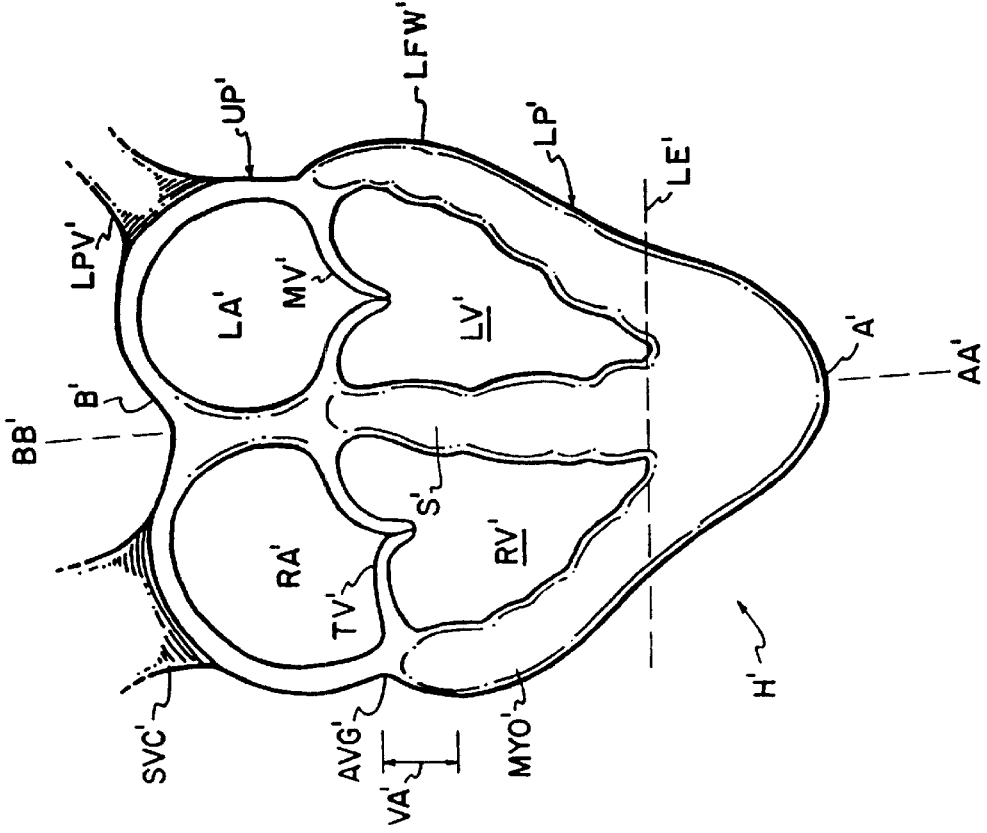
FIG. I

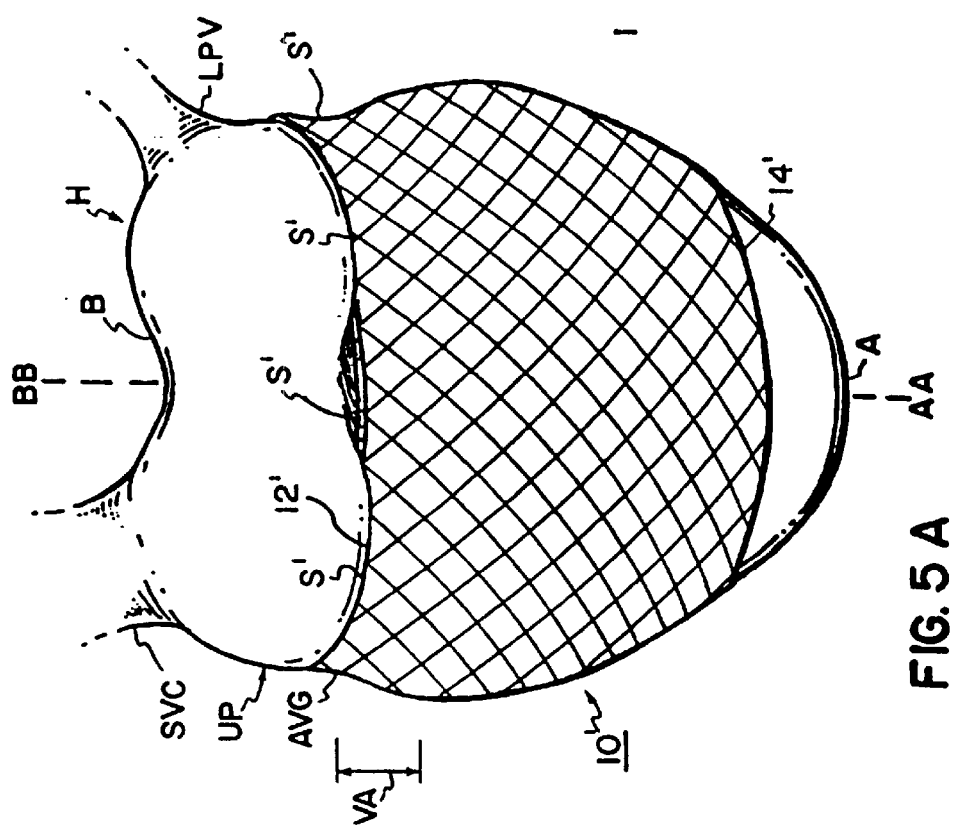
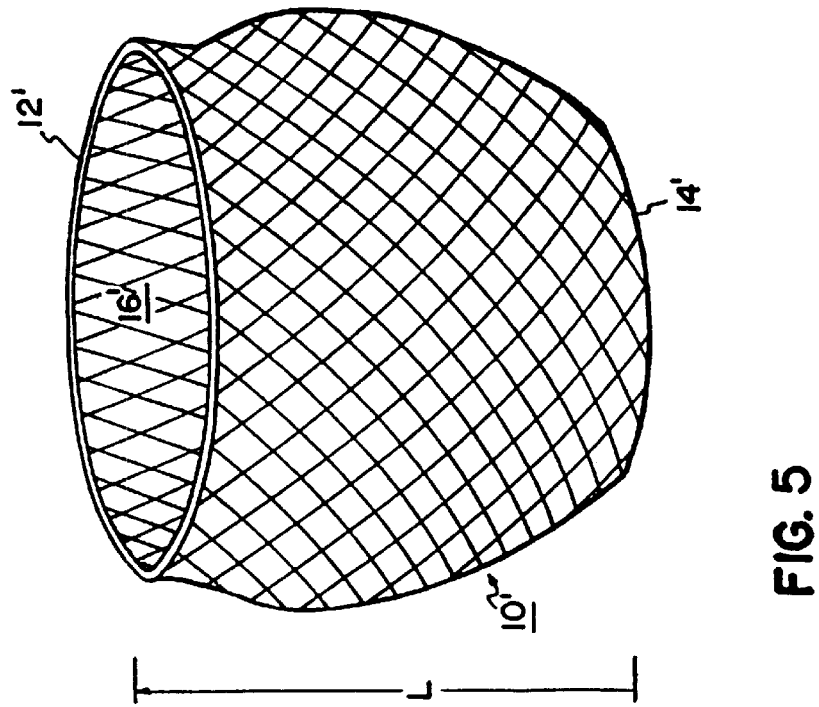
FIG. 5A
FIG. 5

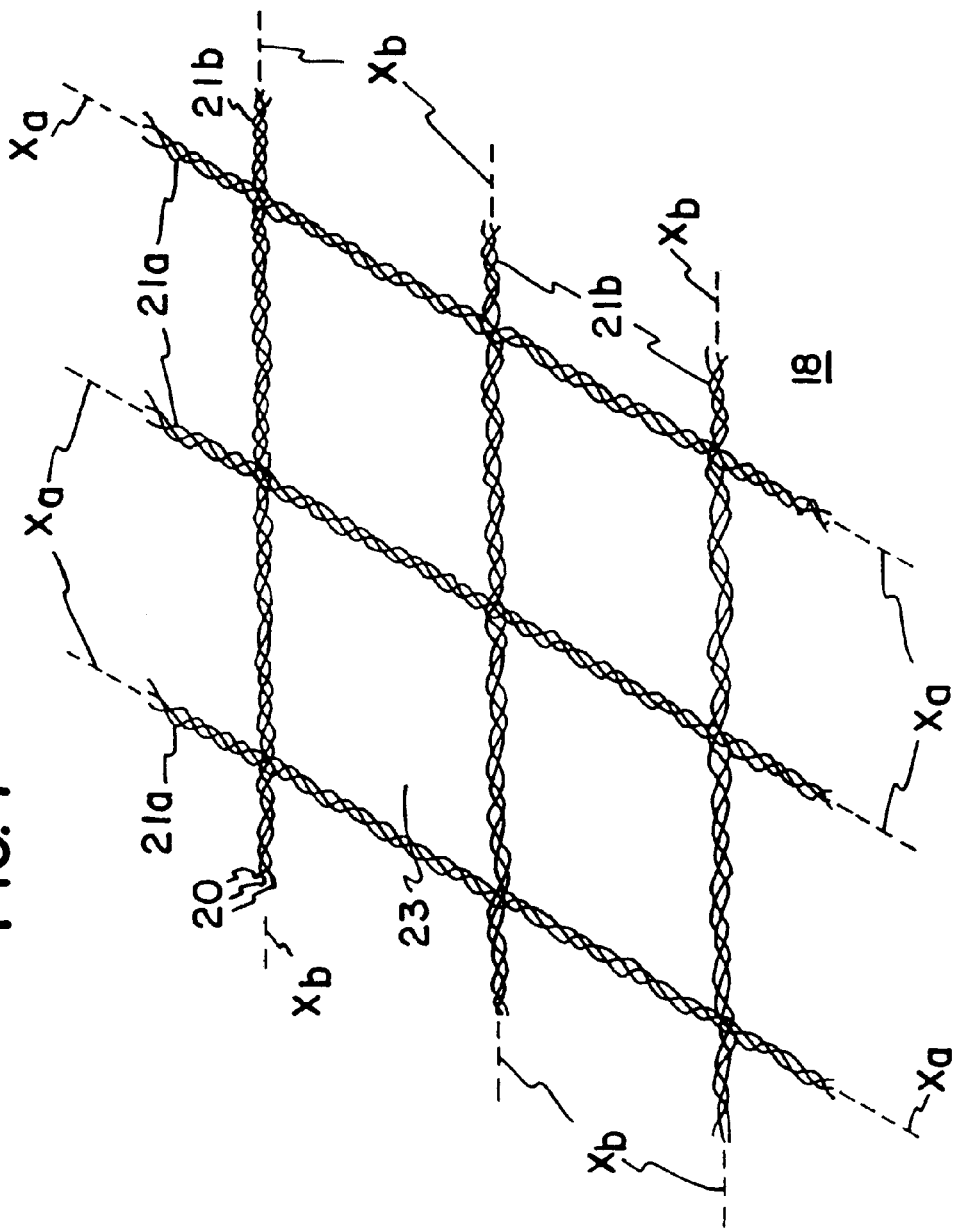

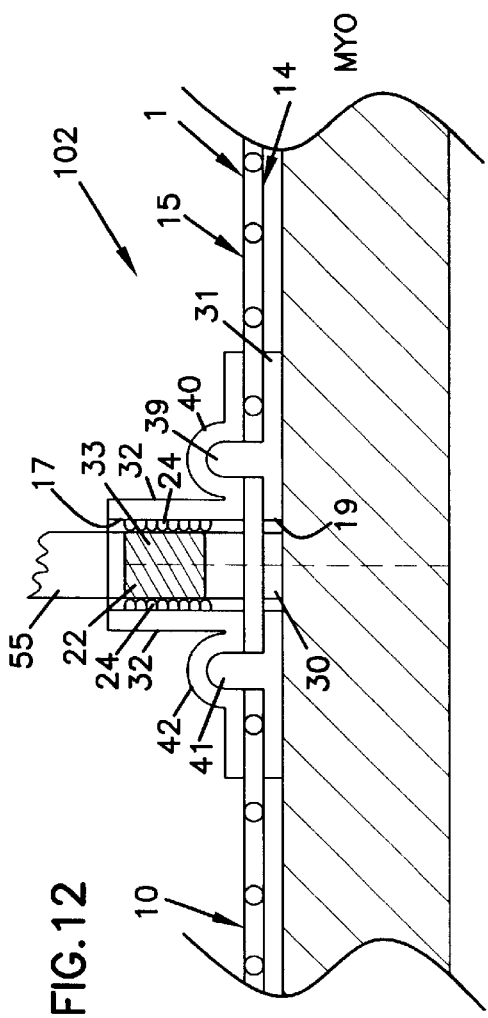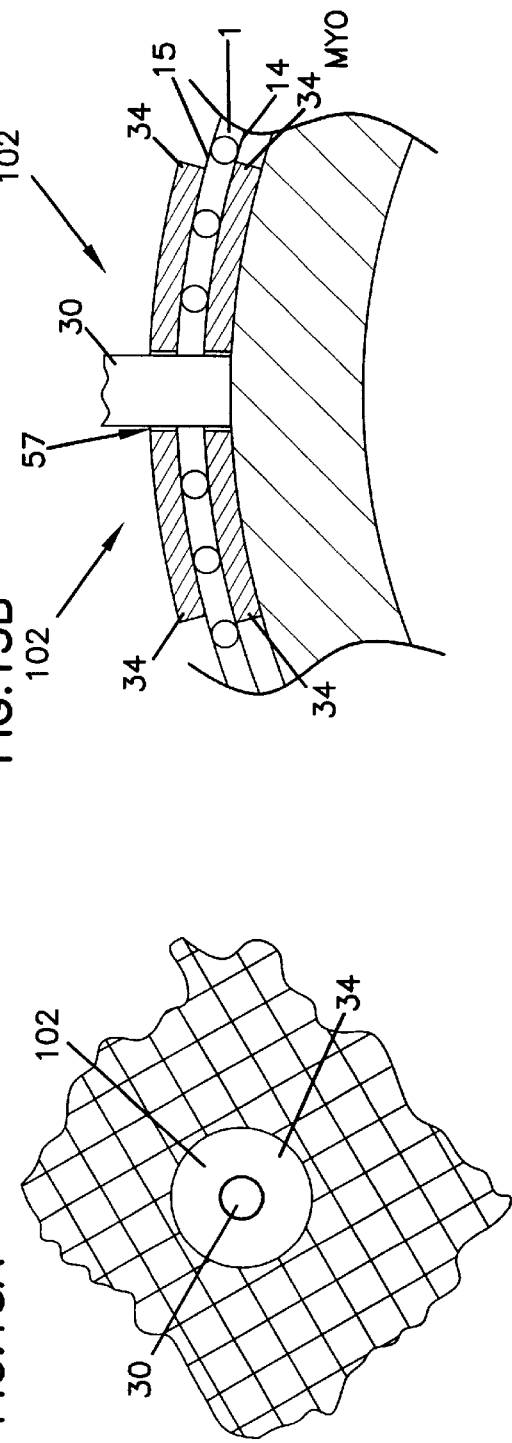

CARDIAC DISEASE TREATMENT AND DEVICE

BACKGROUND OF THE INVENTION

1. Field of the Invention

The present invention pertains to a device and method for treating heart disease. More particularly, the present invention is directed to a method and device for treating congestive heart disease, intraventricular conductance delays, and related valvular dysfunction.

2. Description of the Prior Art

Congestive heart disease is a progressive and debilitating illness. The disease is characterized by a progressive enlargement of the heart.

As the heart enlarges, the heart is performing an increasing amount of work in order to pump blood each heart beat. In time, the heart becomes so enlarged the heart cannot adequately supply blood. An afflicted patient is fatigued, unable to perform even simple exerting tasks and experiences pain and discomfort. Further, as the heart enlarges, the internal heart valves cannot adequately close. This impairs the function of the valves and further reduces the heart's ability to supply blood.

Patients suffering from congestive heart disease are commonly grouped into four classes (i.e., Classes I, II, III and IV). In the early stages (e.g., Classes I and II), drug therapy is the commonly proscribed treatment. The only permanent treatment for congestive heart disease is heart transplant. To qualify, a patient must be in the later stage of the disease (e.g., Classes III and IV with Class IV patients given priority for transplant). Unfortunately, not enough hearts are available for transplant to meet the needs of congestive heart disease patients.

Not surprising, substantial effort has been made to find alternative treatments for congestive heart disease. Recently, a new surgical procedure has been developed. Referred to as the Batista procedure, the surgical technique includes dissecting and removing portions of the heart in order to reduce heart volume. This is a radical new and experimental procedure subject to substantial controversy. Furthermore, the procedure is highly invasive, risky and expensive and commonly includes other expensive procedures (such as a concurrent heart valve replacement). Also, the treatment is limited to Class IV patients and, accordingly, provides no hope to patients facing ineffective drug treatment prior to Class IV. Finally, if the procedure fails, emergency heart transplant is the only available option.

Cardiomyoplasty is a recently developed treatment for earlier stage congestive heart disease (e.g., as early as Class III dilated cardiomyopathy). In this procedure, the latissimus dorsi muscle (taken from the patient's shoulder) is wrapped around the heart and chronically paced synchronously with ventricular systole. Pacing of the muscle results in muscle contraction to assist the contraction of the heart during systole.

While cardiomyoplasty has resulted in symptomatic improvement, the nature of the improvement is not understood. For example, one study has suggested the benefits of cardiomyoplasty are derived less from active systolic assist than from remodeling, perhaps because of an external elastic constraint. The study suggests an elastic constraint (i.e., a non-stimulated muscle wrap or an artificial elastic sock placed around the heart) could provide similar benefits. Kass et al., *Reverse Remodeling From Cardiomyoplasty In Human Heart Failure: External Constraint Versus Active Assist*, 91 *Circulation* 2314–2318 (1995).

Even though cardiomyoplasty has demonstrated symptomatic improvement, studies suggest the procedure only minimally improves cardiac performance. The procedure is highly invasive requiring harvesting a patient's muscle and an open chest approach (i.e., sternotomy) to access the heart. Furthermore, the procedure is expensive—especially those using a paced muscle. Such procedures require costly implantable sources. The cardiomyoplasty procedure is complicated. For example, it is difficult to adequately wrap the muscle around the heart with a satisfactory fit. Also, if adequate blood flow is not maintained to the wrapped muscle, the muscle may necrose. The muscle may stretch after wrapping reducing its constraining benefits and is generally not susceptible to post-operative adjustment. Finally, the muscle may fibrose and adhere to the heart causing undesirable constraint on the contraction of the heart during systole.

In addition to cardiomyoplasty, mechanical assist devices have been developed as intermediate procedures for treating congestive heart disease. Such devices include left ventricular assist devices ("LVAD") and total artificial hearts ("TAH"). An LVAD includes a mechanical pump for urging blood flow from the left ventricle and into the aorta. An example of such is shown in U.S. Pat. No. 4,995,857 to Arnold dated Feb. 26, 1991. LVAD surgeries are still in U.S. clinical trials and not generally available. Such surgeries are expensive. The devices are at risk of mechanical failure and frequently require external power supplies. TAH devices, such as the celebrated Jarvik heart, are used as temporary measures while a patient awaits a donor heart for transplant.

Other attempts at cardiac assist devices are found in U.S. Pat. No. 4,957,477 to Lundbäck dated Sep. 18, 1990, U.S. Pat. No. 5,131,905 to Grooters dated Jul. 21, 1992 and U.S. Pat. No. 5,256,132 to Snyders dated Oct. 26, 1993. Both of the Grooters and Snyders patents teach cardiac assist devices which pump fluid into chambers opposing the heart to assist systolic contractions of the heart. The Lundbäck patent teaches a double-walled jacket surrounding the heart. A fluid fills a chamber between the walls of the jacket. The inner wall is positioned against the heart and is pliable to move with the heart. Movement of the heart during beating displaces fluid within the jacket chamber.

Additionally, cardiac failure patients may suffer from long intraventricular conduction delays. Generally, such delays result in a slow uncoordinated contraction, resulting in poor ejection of blood from the ventricle. Inefficient ejection can lead to poor cardiac output and an increased end-diastolic volume. Increased end-diastolic volume can result in increased ventricular wall stress and stretching of the myocardium. This, in turn, may stimulate ventricular dilation and ventricular remodeling, starting a progressive heart failure spiral.

Pacing systems that stimulate heart muscle contraction with precisely timed discharges of electricity are available. Pacing has been used to resynchronize ventricular contraction, thereby increasing the efficiency of ventricular contraction, reducing end-diastolic volume and slowing the heart failure progression.

Pacing systems that pace the right ventricle (RV) and the left ventricle (LV) simultaneously via a transvenous lead introduced through the cardiac veins are available. Additionally, a left ventricular epicardial lead combined with a right ventricular lead has been used for biventricular pacing. However, when only a single point on the left ventricle is paced, delayed conduction in the left ventricle may result in a poorly synchronized contraction (i.e., part of the ventricle contracts while other portions are not contracting). This can result in a dyskinetic bulging in the non-contracting section.

Thus, selection of the left ventricular stimulation site is critical in achieving good clinical outcomes. Ideally several points on the left ventricular wall are paced to assure the most coordinated contraction. However, pacing from various or multiple sites on the left ventricle is difficult. Positioning one transvenous lead through the cardiac veins is difficult, much less positioning multiple leads. Additionally, current epicardial electrodes are screwed or sewn into or onto the epicardium. This may cause damage to the heart or create chronic exit block (high pacing energy required to simulate through the resultant scar tissue, ultimately energy greater than implantable source can apply so no stimulation occurs), particularly if multiple epicardial electrodes are used.

Commonly assigned U.S. Pat. No. 5,702,343 to Alferness dated Dec. 30, 1997 teaches a jacket to constrain cardiac expansion during diastole. The present invention pertains to improvements to the invention disclosed in the '343 patent.

SUMMARY OF THE INVENTION

The invention provides a device for treating cardiac disease. The device includes biologically compatible material, an electrotherapy instrument, and a placement apparatus capable of removably attaching a lead of the electrotherapy instrument to the biologically compatible material. In one embodiment, the biologically compatible material is a patch that is configured to be secured to the epicardial surface of the heart. In an alternate embodiment, the biologically compatible material is constructed as a jacket of flexible material designed to be secured to the heart, such as the jackets described in U.S. Pat. Nos., 5,702,343 and 6,123,662. The disclosures of both patents are hereby incorporated by reference herein in their entirety.

In one embodiment, the electrotherapy instrument is a cardiac pacing device. In another embodiment, the electrotherapy instrument is a defibrillating device.

According to the invention, the electrotherapy device includes at least one lead that has at least one electrode. The placement apparatus is configured to position the electrode in electrical contact with a patient's heart, typically the myocardium of the heart. If desired, the electrotherapy instrument can have more than one lead.

Various configurations for a placement apparatus are provided. In some embodiments, the placement apparatus is initially secured to the cardiac reinforcement device. In other embodiments, the placement apparatus is initially secured to the lead.

Examples of a placement apparatus that is initially secured to the cardiac reinforcement device include a placement apparatus configured as a snap having a base and a cap, each of which define an opening capable of housing a lead. In an alternate embodiment, the placement apparatus is constructed as a non-conductive pad that defines an opening capable of housing a lead.

Examples of a placement apparatus that is initially secured to the lead include a placement apparatus constructed as at least one projection secured to said lead, typically, a plurality of projections extending radially outward from said lead. Alternately, the placement apparatus is constructed as a flange extending radially outward from said lead. The placement apparatus can also be threads coiled along a distal end of the lead, such that the threads engage fibers of the biologically compatible material to secure the lead to the biologically compatible material.

The invention also provides methods for treating cardiac disease by implanting the above-described device. According to the invention, the desired location of the electrode on the cardiac surface can be determined by stimulating various locations on the cardiac surface and observing cardiac response (e.g., contractile efficiency). According to one method of the invention, the cardiac response due to electrical stimulation at various locations on the heart is tested prior to securing the lead(s) to the cardiac reinforcement device. Advantageously, the device of the invention provides various placement apparatus(es) such that the lead(s) can be secured at a location that provides a desired cardiac response.

In another embodiment, the locations for cardiac stimulation can be tested by releasably securing the lead to the cardiac reinforcement device using at least one placement apparatus. The placement apparatus(es) permit easy attachment and removal of the electrode(s) so that various positions on the heart can be tested. Once the desired location(s) is/are determined, the lead(s) is/are secured to the cardiac reinforcement device. If desired, the lead can be secured to the cardiac reinforcement device using the placement apparatus. Alternately, or additionally, the lead(s) is/are secured to the cardiac reinforcement device by suturing or gluing the lead in place.

BRIEF DESCRIPTION OF THE DRAWINGS

FIG. 1 is a schematic cross-sectional view of a normal, healthy human heart shown during systole;

FIG. 1A is the view of FIG. 1 showing the heart during diastole;

FIG. 5 is a perspective view of a second embodiment of a cardiac reinforcement device;

FIG. 5A is a side elevation view of a diseased heart in diastole with the device of FIG. 5 in place;

FIG. 7 is an enlarged view of a knit construction of the device of the present invention in a rest state;

FIG. 12 is a cross sectional view of a placement apparatus according to the invention;

FIG. 13A is a top view of a placement apparatus according to the invention;

FIG. 13B is a cross sectional view of the placement apparatus of FIG. 13A;

DESCRIPTION OF THE PREFERRED EMBODIMENT

1. A Healthy Heart

Figure 2:
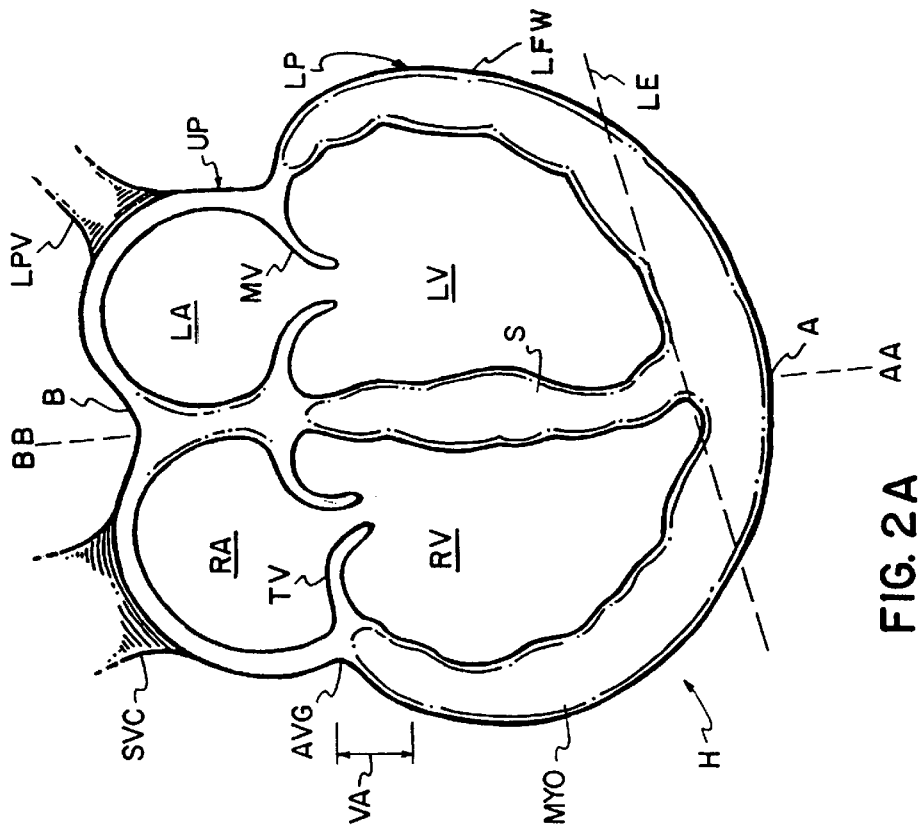
FIG. 2 is a schematic cross-sectional view of a diseased human heart shown during systole.

With initial reference to FIGS. 1 and 1A, a normal, healthy human heart H' is schematically shown in cross-section and will now be described in order to facilitate an understanding of the present invention. In FIG. 1, the heart H' is shown during systole (i.e., high left ventricular pressure). In FIG. 1A, the heart H' is shown during diastole (i.e., low left ventricular pressure).

The heart H' is a muscle having an outer wall or myocardium MYO' and an internal wall or septum S'. The myocardium MYO' and septum S' define four internal heart chambers including a right atrium RA', a left atrium LA', a right ventricle RV' and a left ventricle LV'. The heart H' has a length measured along a longitudinal axis AA'–BB' from an upper end or base B' to a lower end or apex A'.

The right and left atria RA', LA' reside in an upper portion UP' of the heart H' adjacent the base B'. The right and left ventricles RV', LV' reside in a lower portion LP' of the heart H' adjacent the apex A'. The ventricles RV', LV' terminate at ventricular lower extremities LE' adjacent the apex A' and spaced therefrom by the thickness of the myocardium MYO'.

Due to the compound curves of the upper and lower portions UP', LP', the upper and lower portions UP', LP' meet at a circumferential groove commonly referred to as the A-V groove AVG'. Extending away from the upper portion UP' are a plurality of major blood vessels communicating with the chambers RA', RV', LA', LV'. For ease of illustration, only the superior vena cava SVC' and a left pulmonary vein LPV' are shown as being representative.

The heart H' contains valves to regulate blood flow between the chambers RA', RV', LA', LV' and between the chambers and the major vessels (e.g., the superior vena cava SVC' and a left pulmonary vein LPV'). For ease of illustration, not all of such valves are shown. Instead, only the tricuspid valve TV' between the right atrium RA' and right ventricle RV' and the mitral valve MV' between the left atrium LA' and left ventricle LV' are shown as being representative.

The valves are secured, in part, to the myocardium MYO' in a region of the lower portion LP' adjacent the A-V groove AVG' and referred to as the valvular annulus VA'. The valves TV' and MV' open and close through the beating cycle of the heart H.

FIGS. 1 and 1A show a normal, healthy heart H' during systole and diastole, respectively. During systole (FIG. 1), the myocardium MYO' is contracting and the heart assumes a shape including a generally conical lower portion LP'. During diastole (FIG. 1A), the heart H' is expanding and the conical shape of the lower portion LP' bulges radially outwardly (relative to axis AA'–BB').

The motion of the heart H' and the variation in the shape of the heart H' during contraction and expansion is complex. The amount of motion varies considerably throughout the heart H'. The motion includes a component which is parallel to the axis AA'–BB' (conveniently referred to as longitudinal expansion or contraction). The motion also includes a component perpendicular to the axis AA'–BB' (conveniently referred to as circumferential expansion or contraction).

2. A Diseased Heart

Having described a healthy heart H' during systole (FIG. 1) and diastole (FIG. 1A), comparison can now be made with a heart deformed by congestive heart disease. Such a heart H is shown in systole in FIG. 2 and in diastole in FIG. 2A. All elements of diseased heart H are labeled identically with similar elements of healthy heart H' except only for the omission of the apostrophe in order to distinguish diseased heart H from healthy heart H'.

Comparing FIGS. 1 and 2 (showing hearts H' and H during systole), the lower portion LP of the diseased heart H has lost the tapered conical shape of the lower portion LP' of the healthy heart H'. Instead, the lower portion LP of the diseased heart H bulges outwardly between the apex A and the A-V groove AVG. So deformed, the diseased heart H during systole (FIG. 2) resembles the healthy heart H' during diastole (FIG. 1A). During diastole (FIG. 2A), the deformation is even more extreme.

Figure 2A:
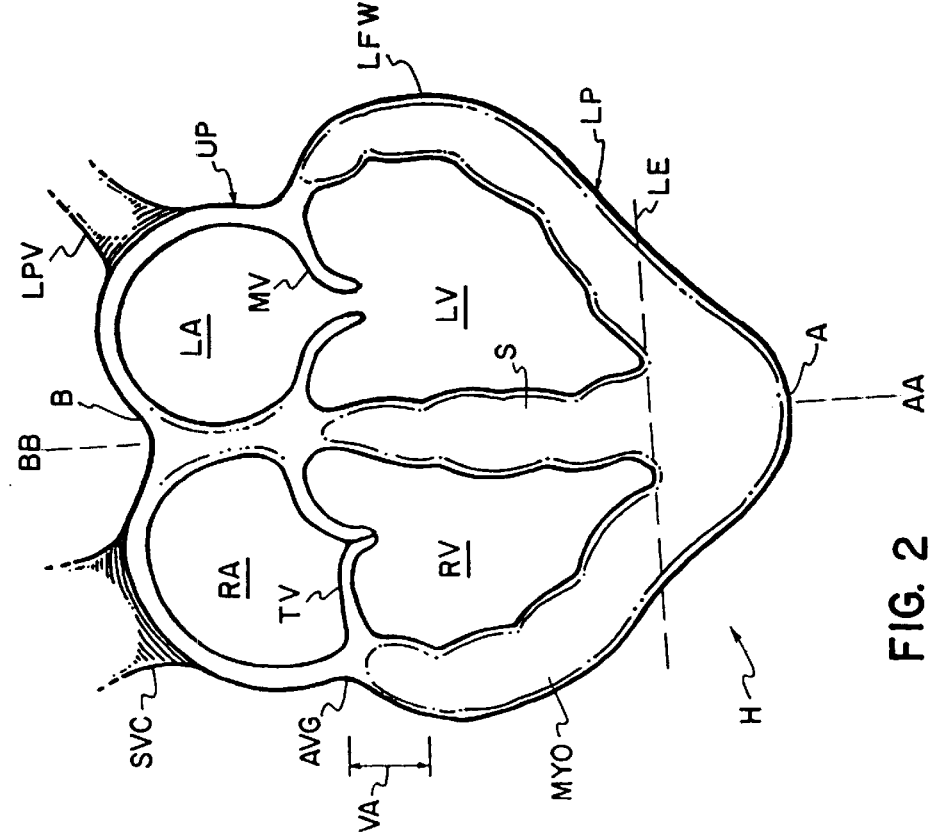
FIG. 2A is the view of FIG. 2 showing the heart during diastole.

As a diseased heart H enlarges from the representation of FIGS. 1 and 1A to that of FIGS. 2 and 2A, the heart H becomes a progressively inefficient pump. Therefore, the heart H requires more energy to pump the same amount of blood. Continued progression of the disease results in the heart H being unable to supply adequate blood to the patient's body and the patient becomes symptomatic insufficiency.

For ease of illustration, the progression of congestive heart disease has been illustrated and described with reference to a progressive enlargement of the lower portion LP of the heart H. While such enlargement of the lower portion LP is most common and troublesome, enlargement of the upper portion UP may also occur.

In addition to cardiac insufficiency, the enlargement of the heart H can lead to valvular disorders. As the circumference of the valvular annulus VA increases, the leaflets of the valves TV and MV may spread apart. After a certain amount of enlargement, the spreading may be so severe the leaflets cannot completely close (as illustrated by the mitral valve MV in FIG. 2A). Incomplete closure results in valvular regurgitation contributing to an additional degradation in cardiac performance. While circumferential enlargement of the valvular annulus VA may contribute to valvular dysfunction as described, the separation of the valve leaflets is most commonly attributed to deformation of the geometry of the heart H. This is best described with reference to FIGS. 1B and 2B.

Figure 2B:
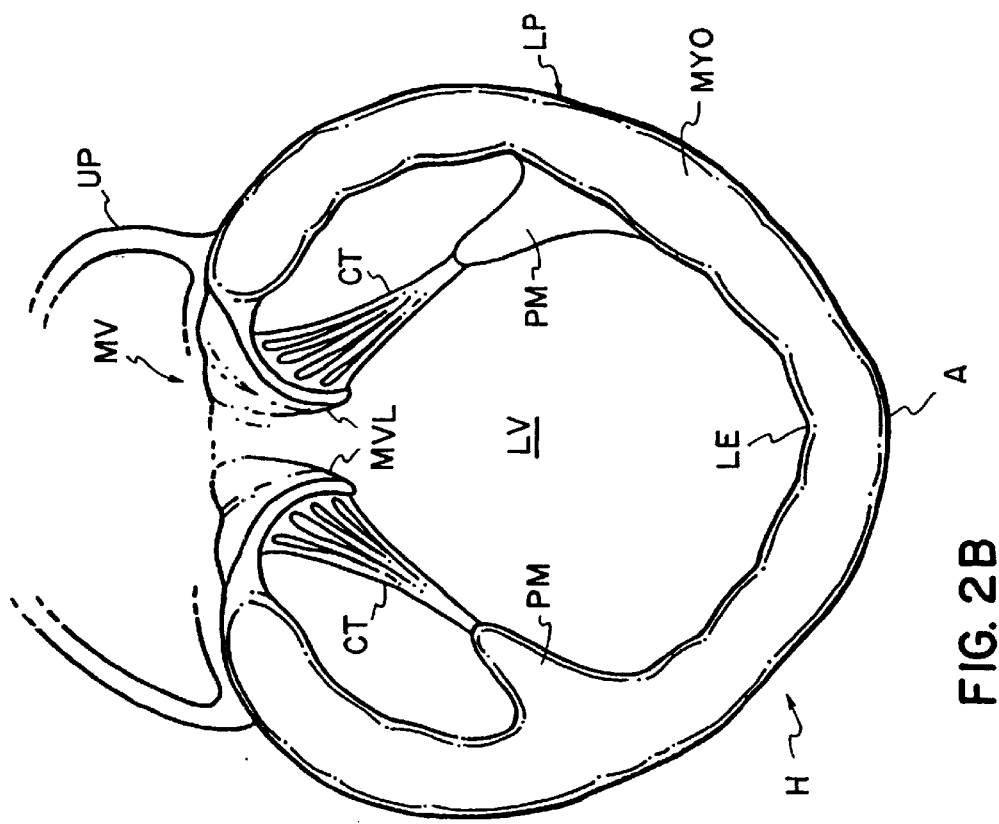
FIG. 2B is the view of FIG. 1B showing a diseased heart.
Figure 1B:
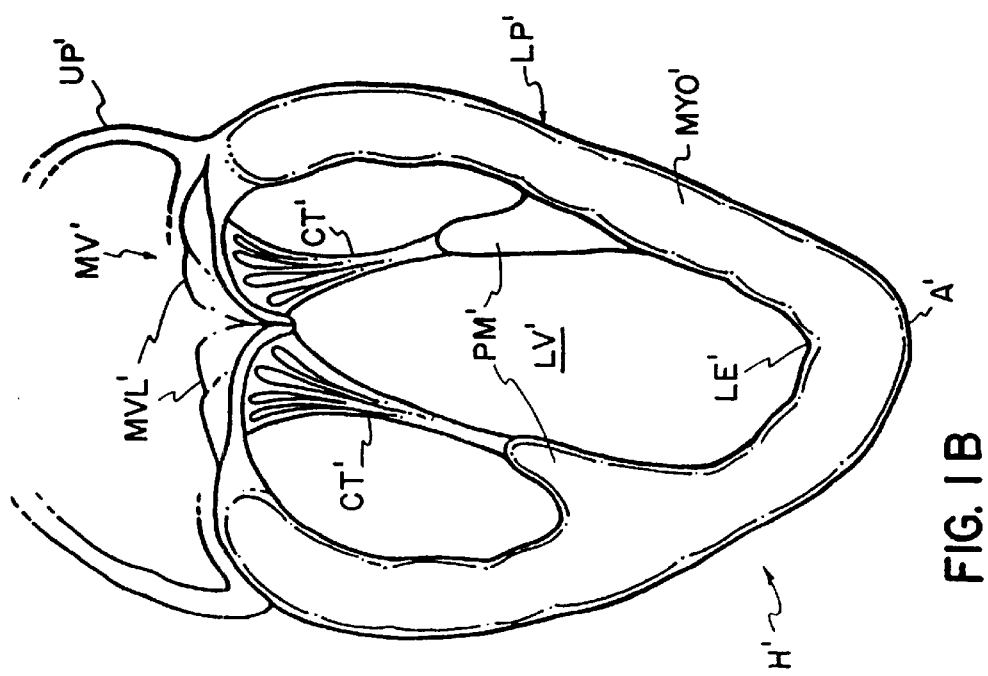
FIG. 1B is a view of a left ventricle of a healthy heart as viewed from a septum and showing a mitral valve.

FIGS. 1B and 2B show a healthy and diseased heart, respectively, left ventricle LV', LV during systole as viewed from the septum (not shown in FIGS. 1B and 2B). In a healthy heart H', the leaflets MVL' of the mitral valve MV' are urged closed by left ventricular pressure. The papillary muscles PM', PM are connected to the heart wall MYO', MYO, near the lower ventricular extremities LE', LE. The papillary muscles PM', PM pull on the leaflets MVL', MVL via connecting chordae tendineae CT', CT. Pull of the leaflets by the papillary muscles functions to prevent valve leakage in the normal heart by holding the valve leaflets in a closed position during systole. In the significantly diseased heart H, the leaflets of the mitral valve may not close sufficiently to prevent regurgitation of blood from the ventricle LV to the atrium during systole.

As shown in FIG. 1B, the geometry of the healthy heart H' is such that the myocardium MYO', papillary muscles PM' and chordae tendineae CT' cooperate to permit the mitral valve MV' to fully close. However, when the myocardium MYO bulges outwardly in the diseased heart H (FIG. 2B), the bulging results in displacement of the papillary muscles PM. This displacement acts to pull the leaflets MVL to a displaced position such that the mitral valve cannot fully close.

Having described the characteristics and problems of congestive heart disease, the treatment method and apparatus of the present invention will now be described.

3. Cardiac Reinforcement Device

Figure 3:
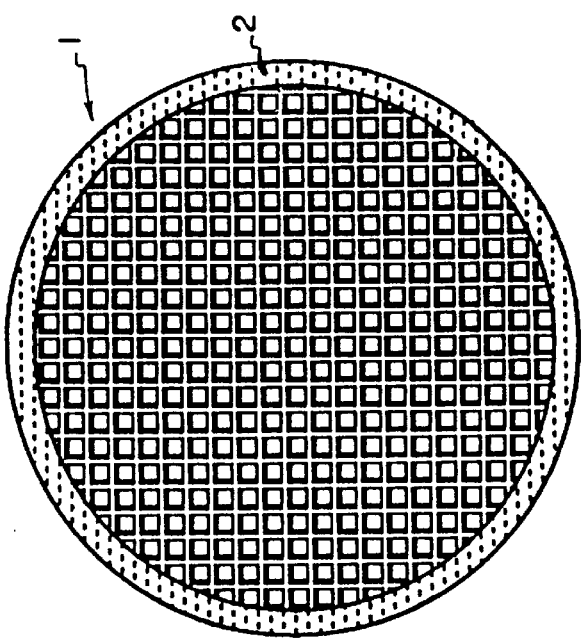
FIG. 3 is a top view of a cardiac reinforcement device configured as a patch.

In one embodiment, (shown in FIG. 3) the device of the invention includes a cardiac reinforcement device 1 configured as a "patch." If desired, the patch can provide for local constraint of the heart wall during cardiac expansion, for example, to reinforce the heart wall damaged by a cardiac aneurysm, myocardial infarction or dyskinetic bulging due to poorly synchronized contraction. Preferably the patch is prepared from a biomedical material. More preferably, the patch is constructed from an open mesh material.

A patch is typically applied to the epicardial surface by suturing around the periphery of the patch. The peripheral edge of the patch can include a thickened "ring" or other reinforcement 2 to enhance the strength of the patch at the point of suture attachment to the epicardium.

In another embodiment, the cardiac reinforcement device 1 is constructed as a jacket 10 configured to surround the myocardium MYO of a heart. As used herein, "surround" means that jacket provides reduced expansion of the heart wall during diastole by applying constraining surfaces at least at diametrically opposing aspects of the heart. In some embodiments, the diametrically opposed surfaces are interconnected, for example, by a continuous material that can substantially encircle the external surface of the heart.

Figure 4A:
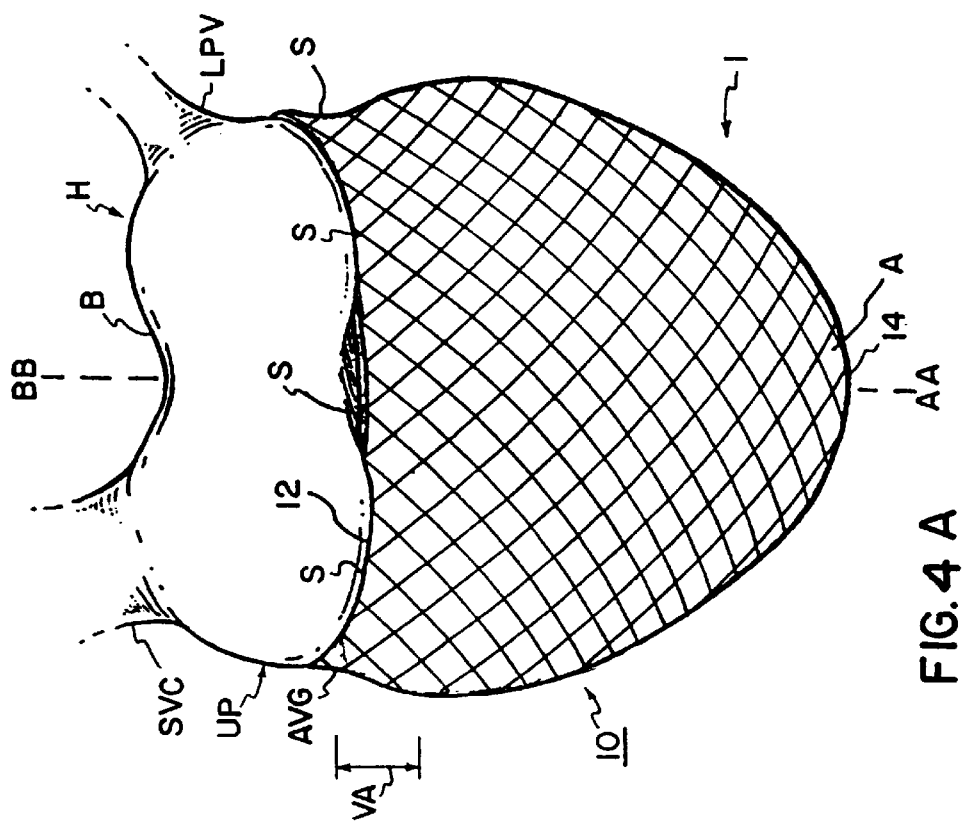
FIG. 4A is a side elevation view of a diseased heart in diastole with the device of FIG. 4 in place.
Figure 4:
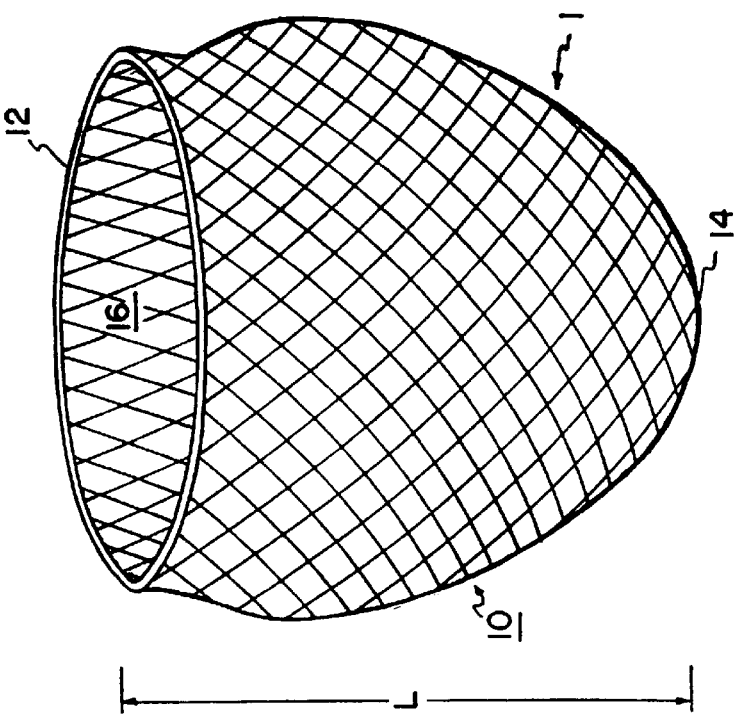
FIG. 4 is a perspective view of a first embodiment of a cardiac reinforcement device.

With reference now to FIGS. 4, 4A, 5 and 5A, the cardiac reinforcement device 1 is shown as a jacket 10 of flexible, biologically compatible material. The jacket 10 is an enclosed knit material having upper and lower ends 12, 14. The jacket 10, 10' defines an internal volume 16, 16' which is completely enclosed but for the open ends 12, 12' and 14'. In the embodiment of FIG. 4, lower end 14 is closed. In the embodiment of FIG. 5, lower end 14' is open. In both embodiments, upper ends 12, 12' are open. Elements in common between the embodiments of FIGS. 4 and 5 are numbered identically with the addition of an apostrophe to distinguish the second embodiment and such elements need not be separately discussed.

The jacket 10 is dimensioned with respect to a heart H to be treated. Specifically, the jacket 10 is sized for the heart H to be constrained within the volume 16. The jacket 10 can be slipped around the heart H. The jacket 10 has a length L between the upper and lower ends 12, 14 sufficient for the jacket 10 to constrain the lower portion LP. The upper end 12 of the jacket 10 extends at least to the valvular annulus VA and further extends to the lower portion LP to constrain at least the lower ventricular extremities LE.

Since enlargement of the lower portion LP is most troublesome, in a preferred embodiment, the jacket 10 is sized so that the upper end 12 can reside in the A-V groove AVG. Where it is desired to constrain enlargement of the upper portion UP, the jacket 10 may be extended to cover the upper portion UP.

Sizing the jacket 10 for the upper end 12 to terminate at the A-V groove AVG is desirable for a number of reasons. First, the groove AVG is a readily identifiable anatomical feature to assist a surgeon in placing the jacket 10. By placing the upper end 12 in the A-V groove AVG, the surgeon is assured the jacket 10 will provide sufficient constraint at the valvular annulus VA. The A-V groove AVG and the major vessels act as natural stops for placement of the jacket 10 while assuring coverage of the valvular annulus VA. Using such features as natural stops is particularly beneficial in minimally invasive surgeries where a surgeon's vision may be obscured or limited.

When the parietal pericardium is opened, the lower portion LP is free of obstructions for applying the jacket 10 over the apex A. If, however, the parietal pericardium is intact, the diaphragmatic attachment to the parietal pericardium inhibits its application of the jacket over the apex A of the heart. In this situation, the jacket can be opened along a line extending from the upper end 12' to the lower end 14' of jacket 10'. The jacket can then be applied around the pericardial surface of the heart and the opposing edges of the opened line secured together after placed on the heart. Systems for securing the opposing edges are disclosed in, for example, U.S. Pat. No. 5,702,343, the entire disclosure of which is incorporated herein by reference. The lower end 14' can then be secured to the diaphragm or associated tissues using, for example, sutures, staples, etc.

In the embodiment of FIGS. 4 and 4A, the lower end 14 is closed and the length L is sized for the apex A of the heart H to be received within the lower end 14 when the upper end 12 is placed at the A-V groove AVG. In the embodiment of FIGS. 5 and 5A, the lower end 14' is open and the length L' is sized for the apex A of the heart H to protrude beyond the lower end 14' when the upper end 12' is placed at the A-V groove AVG. The length L' is sized so that the lower end 14' extends beyond the lower ventricular extremities LE such that in both of jackets 10, 10', the myocardium MYO surrounding the ventricles RV, LV is in direct opposition to material of the jacket 10, 10'. Such placement is desirable for the jacket 10, 10' to present a constraint against enlargement of the ventricular walls of the heart H.

After the jacket 10 is positioned on the heart H as described above, the jacket 10 is secured to the heart. Preferably, the jacket 10 is secured to the heart H through sutures. The jacket 10 is sutured to the heart H at suture locations S circumferentially spaced along, the upper end 12. While a surgeon may elect to add additional suture locations to prevent shifting of the jacket 10 after placement, the number of such locations S is preferably limited so that the jacket 10 does not restrict contraction of the heart H during systole.

Figure 6:
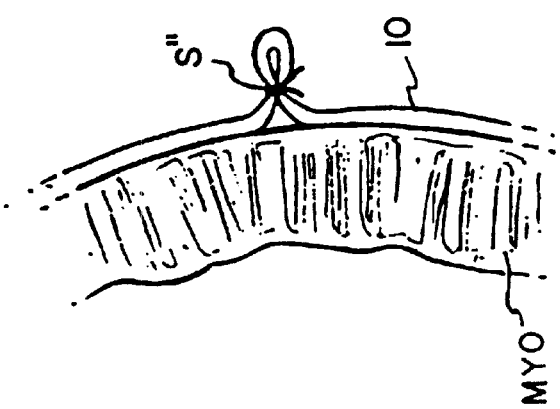
FIG. 6 is a cross-sectional view of a cardiac reinforcement device overlying a myocardium and with the material of the device gathered for a snug fit.

To permit the jacket 10 to be easily placed on the heart H, the volume and shape of the jacket 10 are larger than the lower portion LP during diastole. So sized, the jacket 10 may be easily slipped around the heart H. Once placed, the jacket's volume and shape are adjusted for the jacket 10 to snugly conform to the external geometry of the heart H during diastole. Such sizing is easily accomplished due to the knit construction of the jacket 10. For example, excess material of the jacket 10 can be gathered and sutured S" (FIG. 6) to reduce the volume of the jacket 10 and conform the jacket 10 to the shape of the heart H during diastole.

Such shape represents a maximum adjusted volume. The jacket 10 constrains enlargement of the heart H beyond the maximum adjusted volume while preventing restricted contraction of the heart H during systole. As an alternative to gathering of FIG. 6, the jacket 10 can be provided with other ways of adjusting volume. For example, as disclosed in U.S. Pat. No. 5,702,343, the jacket can be provided with a slot. The edges of the slot can be drawn together to reduce the volume of the jacket.

The jacket 10 is adjusted to a snug fit on the heart H during diastole. Care is taken to avoid tightening the jacket 10 too much such that cardiac function is impaired. During diastole, the left ventricle LV fills with blood. If the jacket 10 is too tight, the left ventricle LV cannot adequately expand and left ventricular pressure will rise. During the fitting of the jacket 10, the surgeon can monitor left ventricular pressure. For example, a well-known technique for monitoring so-called pulmonary wedge pressure uses a catheter placed in the pulmonary artery. The wedge pressure provides an indication of filling pressure in the left atrium LA and left ventricle LV. While minor increases in pressure (e.g., 2–3 mm Hg) can be tolerated, the jacket 10 is snugly fit on the heart H but not so tight as to cause a significant increase in left ventricular pressure during diastole.

As mentioned, the jacket 10 is constructed from a knit, biocompatible material. The knit 18 is illustrated in FIG. 7. Preferably, the knit is a so-called "Atlas knit" well known in the fabric industry. The Atlas knit is described in Paling, *Warp Knitting Technology*, p. 111, Columbine Press (Publishers) Ltd., Buxton, Great Britain (1970).

The Atlas knit is a knit of fibers 20 having directional expansion properties. More specifically, the knit 18, although formed of generally inelastic fibers 20, permits a construction of a flexible fabric at least slightly expandable beyond a rest state. FIG. 7 illustrates the knit 18 in a rest state. The fibers 20 of the fabric 18 are woven into two sets of fiber strands 21a, 21b having longitudinal axes $X_a$ and $X_b$. The strands 21a, 21b are interwoven to form the fabric 18 with strands 21a generally parallel and spaced-apart and with strands 21b generally parallel and spaced-apart.

Figure 8:
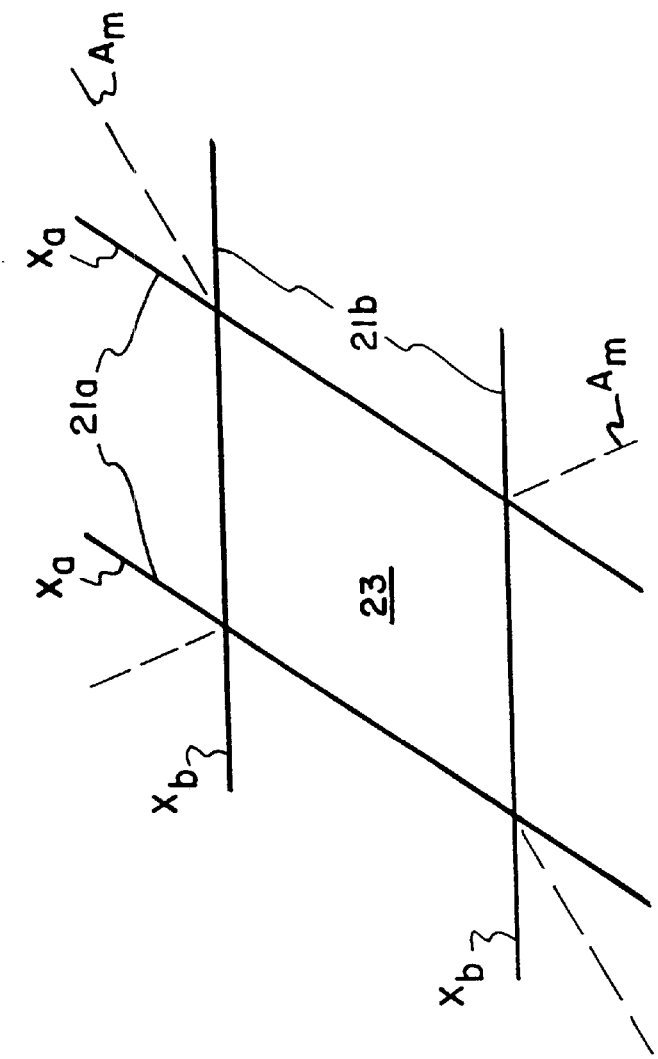
FIG. 8 is a schematic view of the material of FIG. 7.

For ease of illustration, fabric 18 is schematically shown in FIG. 8 with the axis of the strands 21a, 21b only being shown. The strands 21a, 21b are interwoven with the axes $X_a$ and $X_b$ defining a diamond-shaped open cell 23 having diagonal axes $A_m$. In a preferred embodiment, the axes $A_m$ are 5 mm in length when the fabric 18 is at rest and not stretched. The fabric 18 can stretch in response to a force. For any given force, the fabric 18 stretches most when the force is applied parallel to the diagonal axes $A_m$. The fabric 18 stretches least when the force is applied parallel to the strand axes $X_a$ and $X_b$. The jacket 10 is constructed for the material of the knit to be directionally aligned for a diagonal axis $A_m$ to be parallel to the heart's longitudinal axis AA-BB While the jacket 10 is expandable due to the above described knit pattern, the fibers 20 of the knit 18 are preferably non-expandable. While all materials expand to at least a small amount, the fibers 20 are preferably formed of a material with a low modulus of elasticity. In response to the low pressures in the heart H during diastole, the fibers 20 are non-elastic. In a preferred embodiment, the fibers are 70 Denier polyester. While polyester is presently preferred, other suitable materials include polytetrafluoroethylene (PTFE), expanded PTFE (ePTFE), polypropylene and stainless steel.

The knit material has numerous advantages. Such a material is flexible to permit unrestricted movement of the heart H (other than the desired constraint on circumferential expansion). The material is open defining a plurality of interstitial spaces for fluid permeability as well as minimizing the amount of surface area of direct contact between the heart H and the material of the jacket 10 (thereby minimizing areas of irritation or abrasion) to minimize fibrosis and scar tissue.

A large open area for cells 23 is desirable to minimize the amount of surface area of the heart H in contact with the material of the jacket 10 (thereby reducing fibrosis). However, if the cell area 23 is too large, localized aneurysm can form. Also, a strand 21a, 21b can overly a coronary vessel with sufficient force to partially block the vessel. A smaller cell size increases the number of strands thereby decreasing the restricting force per strand. Preferably, a maximum cell area is no greater than about 6.45 cm$^2$ (about 2.54 cm by 2.54 cm) and, more preferably, is about 0.25 cm$^2$ (about 0.5 cm by 0.5 cm). The maximum cell area is the area of a cell 23 after the material of the jacket 10 is fully stretched and adjusted to the maximum adjusted volume on the heart H as previously described.

The fabric 18 is preferably tear and run resistant. In the event of a material defect or inadvertent tear, such a defect or tear is restricted from propagation by reason of the knit construction.

The cardiac reinforcement device 1 is low-cost, easy to place and secure, and is susceptible to use in minimally invasive procedures. The thin, flexible fabric 18 permits the cardiac reinforcement device 1 to be collapsed and passed through a small diameter tube in a minimally invasive procedure.

The jacket 10 can be used in early stages of congestive heart disease. For patients facing heart enlargement due to viral infection, the jacket 10 permits constraint of the heart H for a sufficient time to permit the viral infection to pass. In addition to preventing further heart enlargement, the jacket 10 treats valvular disorders by constraining circumferential enlargement of the valvular annulus and deformation of the ventricular walls.

The jacket 10, including the knit construction, freely permits longitudinal and circumferential contraction of the heart H (necessary for heart function). Unlike a solid wrap (such as a muscle wrap in a cardiomyoplasty procedure), the fabric 18 does not impede cardiac contraction. After fitting, the jacket 10 is inelastic to prevent further heart enlargement while permitting unrestricted inward movement of the ventricular walls. The open cell structure permits access to coronary vessels for bypass procedures subsequent to placement of the jacket 10. Also, in cardiomyoplasty, the latissimus dorsi muscle has a variable and large thickness (ranging from about 1 mm to 1 cm). The material of the jacket 10 is uniformly thin (less than 1 mm thick). The thin wall construction is less susceptible to fibrosis and minimizes interference with cardiac contractile function.

In addition to the foregoing, the present invention can be used to reduce heart size at the time of placement in addition to preventing further enlargement. For example, the device can be placed on the heart and sized snugly to urge the heart to a reduced size. More preferably, the heart size can be reduced at the time of jacket placement through drugs (e.g., dobutamine, dopamine or epinephrine or any other positive inotropic agents) to reduce the heart size. The jacket of the present invention is then snugly placed on the reduced sized heart and prevents enlargement beyond the reduced size.

Modifications of the cardiac reinforcement device 1 are forseen, and meant to be included within the scope of the invention. For example, the jacket 10 need not be directly applied to the epicardium (i.e., outer surface of the myocardium) but could be placed over the parietal pericardium. Further, an anti-fibrosis lining (such as a PTFE coating on the fibers of the knit) could be placed between the heart H and the jacket 10. Alternatively, the fibers 20 can be coated with PTFE.

According to the invention, a cardiac reinforcement device 1, is combined with electrotherapy. As used herein, the term "electrotherapy" refers to the delivery an electrical impulse to a patient's heart, including both cardiac pacing therapy and defibrillation therapy. Electrotherapy can also include the transmission of a signal from the heart to a receiving device capable of "reading" the signal, for example, to monitor the activity and/or physiology of the heart.

4. Cardiac Pacing Therapy

The invention provides a cardiac reinforcement device 1 in combination with an instrument for electrotherapy. One example of electrotherapy is cardiac pacing therapy.

Figure 9:
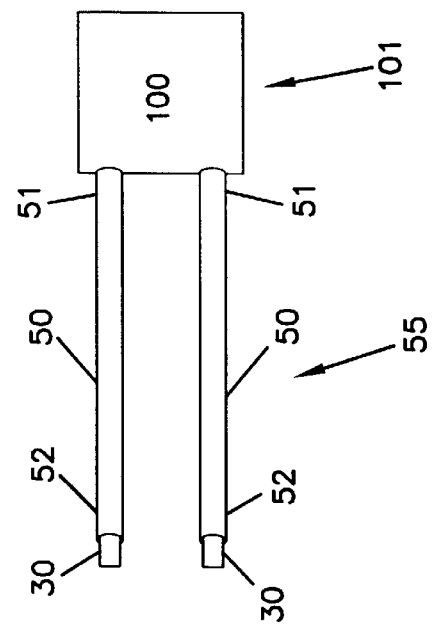
FIG. 9 is a schematic view of a cardiac pacing device.

FIG. 9 provides a schematic representation of an instrument for electrotherapy 101, such as a cardiac pacing device. Typically, a cardiac pacing device includes an implantable source 100 capable of generating an electric impulse and at least one lead 55. The implantable source 100 typically includes programmable electronic circuitry and a battery. The lead 55 delivers the electronic pulses to the heart H (typically the myocardium MYO of the heart H).

The lead 55 can also carry signals back to the implantable source 100 from the heart. By "reading" these signals, the heart's activity can be monitored and therapy can be adjusted appropriately. Thus, also included within the scope of the invention is a cardiac pacing device comprising a plurality of electrodes 30 in which at least one electrode 30 functions as a sensing electrode. Examples of a sensing electrode include an oxygen sensing electrode and a pressure sensing electrode. The sensing electrode 30 may assist in determining a suitable stimulation routine. Such feedback and pacing adjustments could be physician activated (i.e., performed periodically) or automatic (i.e., performed continuously).

Generally, the lead 55 includes at least one conductive element 50, and at least one electrode 30. Generally, the conductive element 50 comprises at least one electrical connector wire (not shown) enclosed within an insulating material, such as polyurethane. The proximate end 51 of the conductive element 50 is operably connected to the implantable source 100. The distal end 52 of the conductive element 50 is operably connected to at least one electrode 30.

The implantable source 100 can be external or implanted subcutaneously, typically below the patient's collarbone or in the patient's abdomen. Typically, the cardiac pacing device is implanted subcutaneously with at least one electrode 30 is in electrical contact with the heart H.

Generally, a pacing system stimulates the heart muscle with precisely timed discharges of electricity to synchronize ventricular contraction. Resynchronization of ventricular contraction can increase the efficiency of ventricular contraction, thereby reducing end-diastolic volume and slowing the heart failure progression.

A cardiac pacing device may incorporate a single electrode 30 or multiple electrodes 30. In a cardiac pacing device having more than one electrode 30, the electrodes are typically spaced from one another and electrically isolated. A skilled physician is capable of determining a suitable location for the electrode(s) 30. For example, the electrode(s) 30 can be located on the left ventricular surface, right ventricular surface, left atrial surface, right atrial surface, or any combination thereof.

According to one embodiment of the invention, a cardiac reinforcement device 1 is combined with cardiac pacing therapy. The cardiac reinforcement device 1 provides support and prevents further dilation of the heart, a problem seen with many biventricular pacing patients. Additionally, support to the ventricular wall by the cardiac reinforcement device 1 reduces dyskinetic bulging during left ventricular stimulation delays. Furthermore, the cardiac reinforcement device 1 may assist in securing the leads 55 to the heart H.

Figure 10:
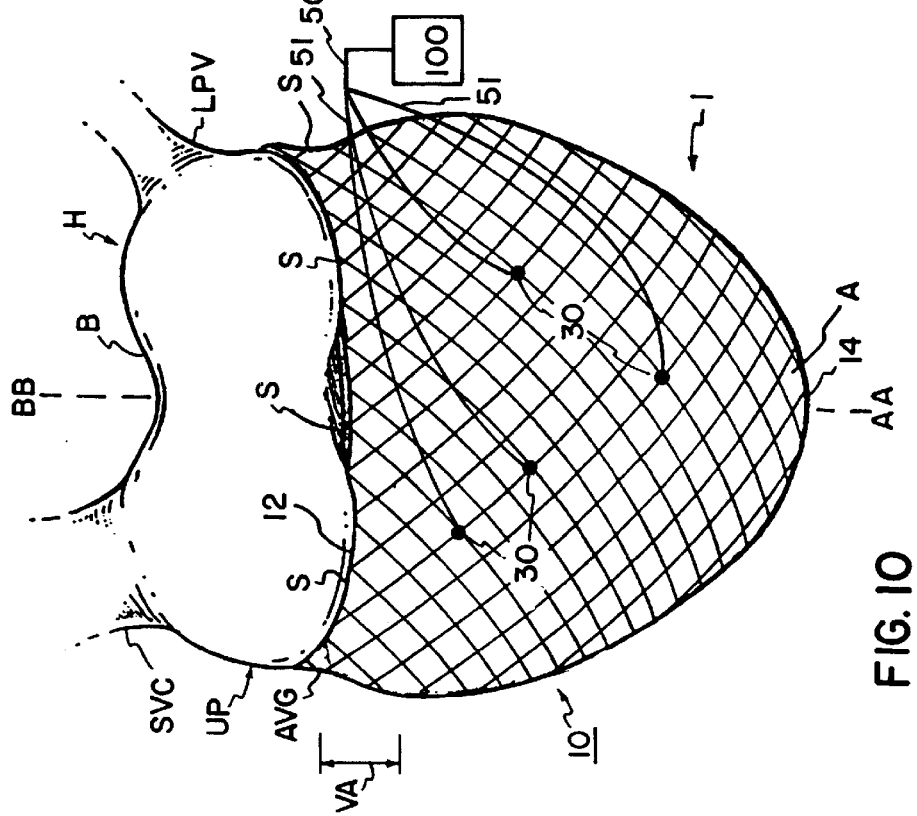
FIG. 10 is a side elevation view of a diseased heart in diastole with the device of the invention in place.

As discussed above, a cardiac pacing device may include a single electrode 30 or multiple electrodes 30. If desired, multiple electrodes 30 can be programmed to transmit electrical impulses simultaneously (FIG. 10). Alternately, the multiple electrodes 30 can be operated with separate functions. For example, electrical impulses can be sent to electrodes 30 in a specific sequence to maximize contractile efficiency. For example, the cardiac pacing device may be configured such that a first electrode (or electrodes) 30 transmits an electrical impulse to a predetermined region of the heart (e.g., the right ventricle RV) to initiate a cardiac depolarization wave and a second electrode (or electrodes) 30 subsequently transmits an electrical impulse to another predetermined region of the heart (e.g., the left ventricle LV). In another example, a plurality of pacing electrodes 30 (e.g., four to six electrodes 30) are evenly spaced over the left ventricular LV free wall LFW to stimulate a coordinated contraction of the left ventricle LV. The LV free wall LFW is the portion of the LV that is opposite the septum S. Sequential stimulation of the multiple electrodes 30 or electrode 30 groups arranged on the left ventricular LV free wall LFW can be used to simulate a normal conduction and contraction pattern.

Figure 11:
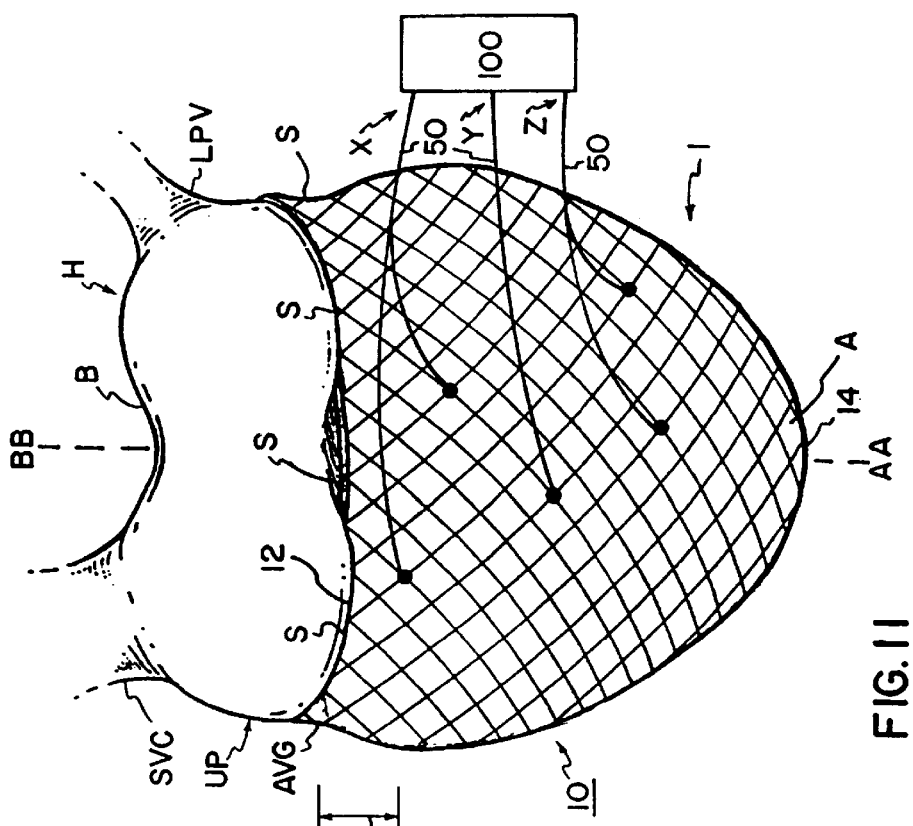
FIG. 11 is a side elevation view of a diseased heart in diastole with the device of the invention in place.

One example of a stimulation sequence is shown in FIG. 11. The implantable source 100 first transmits an electrical impulse down a first lead X, stimulating the electrodes 30 electrically connected to this lead. After a predetermined delay, the implantable source 100 transmits an electrical impulse down a second lead Y, stimulating the electrodes 30 electrically connected to this lead. Finally, an electrical impulse is transmitted down a third lead Z, stimulating the corresponding electrodes 30. This is only one example of a stimulation sequence. Numerous other electrode configurations and stimulation sequences are envisioned.

5. Defibrillation Therapy

The invention also includes a cardiac reinforcement device 1 in combination with defibrillation therapy.

The schematic representation of an electrotherapeutic device in FIG. 9 can also be applied to a defibrillator. Generally, a defibrillator includes an implantable source 100 of a defibrillating waveform and at least a first and second lead 55. Generally, each lead 55 includes at least one conductive element 50, and at least one electrode 30. Generally, the conductive element 50 comprises at least one electrical connector wire (not shown) enclosed within an insulating material, such as polyurethane.

The implantable source 100 typically includes programmable electronic circuitry and a battery. The lead 55 delivers the electronic pulses to the heart H (typically the myocardium MYO of the heart H) and can also carry signals back to the implantable source 100.

Generally, a defibrillation therapy involves the application of a pulse of electricity to a patient's heart to convert ventricular arrythmias, such as ventricular fibrillation and ventricular tachycardia, to normal heart rhythms (i.e., defibrillation and cardioversion, respectively). For effective defibrillation, defibrillation electrodes are preferably located on opposite sides of the heart (for example, on the left lateral and right lateral ventricular epicardium), such that as much cardiac muscle mass as possible is located within the direct current path of the defibrillating shock.

Defibrillators can be external or implanted and are typically implanted in patients who have a high likelihood of needing electrotherapy. Typically, implanted defibrillators monitor the patient's heart activity and automatically supply electrotherapeutic pulses to the patient's heart when necessary.

According to the invention, a cardiac reinforcement device 1 is combined with defibrillation therapy. Cardiac arrythmias are likely to occur patients with heart failure, particularly in patients with dilated hearts. The cardiac reinforcement device 1 is useful for securing the defibrillation electrodes 30 in electrical contact with the heart H. Furthermore, the cardiac reinforcement device I would not interfere with trans chest defibrillation (should the internal system fail) since current easily flows through the mesh.

6. Combination Therapy

According to the invention, the cardiac reinforcement device 1 is configured to releasably secure or position at least one electrode 30 of the instrument for electrotherapy on the heart surface (e.g., the myocardium MYO). The instrument for electrotherapy can be incorporated into the cardiac reinforcement device 1 using a variety of procedures.

For example, a placement apparatus 102 can be secured to the cardiac reinforcement device 1 or the lead 55 of the instrument for electrotherapy, or both. According to the invention, the placement apparatus 102 releasably secures the lead 55 to the cardiac reinforcement device such that the location of the lead can be easily changed, if necessary. In use, the placement apparatus 102 secures the lead 55 to the cardiac reinforcement device 1 such that the electrode 30 is in electrical contact with the heart H.

In one embodiment, the leads 55 are positioned on the cardiac reinforcement device 1 prior to implantation in predetermined positions. In another embodiment, the leads 55 are positioned and secured to the cardiac reinforcement device 1 at the time of implantation, or after the cardiac reinforcement device 1 is secured to the heart H.

In a preferred embodiment, the cardiac reinforcement device 1 positions the electrodes 30 in contact the surface of the heart, without the electrodes 30 penetrating the epicardial surface. Thus, using the cardiac reinforcement device 1 to position the electrodes 30 on the cardiac surface (rather than implanting the electrodes 30 into the epicardium) reduces myocardial damage (as compared conventional epicardial pacing electrodes). If desired, more than one electrode 30 can be positioned on the cardiac surface.

As discussed earlier, selection of the left ventricular stimulation site can affect the clinical outcome. According to one embodiment of the invention, the desired electrode 30 position is determined by stimulating various locations on the cardiac surface and observing cardiac response (e.g., contractile efficiency). If desired, testing for contractile efficiency can be performed prior to implanting the cardiac reinforcement device 1. According to one embodiment, the lead(s) 55 is/are attached to the cardiac reinforcement device in the desired location prior to implantation of the cardiac reinforcement device Alternately, locations for the lead(s) can be tested after the cardiac reinforcement device 1 is placed on the heart H. In one embodiment, the lead 55 is not secured to the cardiac reinforcement device 1 during testing. According to another embodiment, lead 55 is releasably secured to the cardiac reinforcement device 1 during testing, for example, using a placement apparatus 102. The placement apparatus 102 can be secured initially to either the cardiac reinforcement device 1, the lead 55, or both.

In yet another embodiment, the cardiac reinforcement device 1 is provided with a plurality of placement apparatuses 102 at various locations. The heart H is stimulated at one or some, or even all, of the placement apparatus 102 locations to test cardiac response. The lead(s) 55 is/are then secured to the cardiac reinforcement device 1 the placement apparatus 102 location(s) where a suitable cardiac response is obtained.

Once the desired location(s) for cardiac stimulation is/are determined, the lead(s) 55 is/are secured to the cardiac reinforcement device 1. The lead 55 can be secured to the cardiac reinforcement device 1 using a placement apparatus 102. Additionally, or alternately, the lead 55 can be secured to the cardiac reinforcement device 1 by suturing or gluing the lead 55 in place, using, for example, a bioglue. Examples of bioglues include a protein based adhesive, hydrogen, or cyanoacrylate. Additionally, tissue encapsulation of the lead 55 by fibrosis may further assist in securing the lead attachment.

In some embodiments, the placement apparatus 102 is initially secured to the cardiac reinforcement device 1. As used herein, the term "initially secured" means that, at some point prior to implantation, the placement apparatus 102 is secured to the cardiac reinforcement device 1 and not the lead 55. A lead 55 may be secured to the placement apparatus 102 (and hence the cardiac reinforcement device 1) either before or after implantation of the device.

In other embodiments, the placement apparatus 102 is initially secured to the lead 55. A used herein, the term "initially secured" means that, at some point prior to implantation, the placement apparatus 102 is secured to the lead 55 and not the cardiac reinforcement device 1. The lead 55 and placement apparatus 102 may be secured to the cardiac reinforcement device 1 either before or after implantation of the device.

An example of a placement apparatus 102 that is initially secured to the cardiac reinforcement device includes a placement apparatus 102 configured as a snap (FIG. 12). Generally, a snap includes a base 31 and a cap 32. The base 31 and cap 32 both define an opening 17, 19 capable of housing an electrode 30 or conductive element 50 of a lead 55. The "snap" can be constructed from any suitable non-conductive biocompatible material, for example, polyester, polyurethane, polypropylene, PTFE, or other polymeric material.

The base 31 and cap 32 each define an engagement member 39, 40 such that the engagement member 39 of the base 39 is configured to fasten to the engagement member 40 of the cap 32. In one possible embodiment, the engagement member 39 of the base 31 includes at least one stud 41 that is engaged by a clasp 42 defined by the cap 32 to secure the base 31 to the cap 32. In the embodiment shown in FIG. 12, the base 31 is positioned on an interior surface 14 of the cardiac reinforcement device 1 and the cap 32 is secured to the base 31 from an exterior surface 15 of the cardiac reinforcement device 1. As used herein, the term "interior surface" 14 of the cardiac reinforcement device 1 refers to the surface of the device that is proximate the heart when in use. The term "exterior surface" 15 of the cardiac reinforcement device 1 refers to the surface of the device that is opposite the interior surface 14.

If desired, the base 31 can also be secured to an exterior surface 15 of a cardiac reinforcement device 1, for example by sutures (not shown). The lead 55 is secured within the openings 17, 19 defined by the base 31 and cap 32. In one embodiment, the lead 55 includes threads 22 configured to mate with ridges 24 located on the interior surface of the opening defined by the cap 32 (and/or base 31, if desired). According to this embodiment, to secure the lead 55 to the cardiac reinforcement device 1, the lead 55 is rotated as it is urged into the opening 17, 19. Other procedures for securing the lead 55 to the cap 32 can be envisioned, for example, the cap 32 can be crimped around the lead 55.

An alternate embodiment in which the placement apparatus 102 is initially secured to the cardiac reinforcement device 1 is shown in FIGS. 13A and B. In this embodiment, the placement apparatus 102 is configured as a pad 34, secured to the cardiac reinforcement device 1, wherein the pad 34 defines an opening 57 configured to secure the lead 55, conductive element 50 or electrode 30. The pad 34 can be made of any suitable non-conductive biocompatible material, such as polyester, polyurethane, polypropylene, PTFE or other polymeric material. A variety of procedures for securing the pad 34 to the cardiac reinforcement device 1 can be envisioned. For example, the cardiac reinforcement device 1 can be embedded within the pad 34. Alternately, the pad 34 can be sutured to an interior 14 or exterior 15 surface of the cardiac reinforcement device 1. The plug provides reinforcement and is configured to retain the electrode tip. The lead 55 can be secured with the placement apparatus 102 before or after implantation.

Figure 14C:
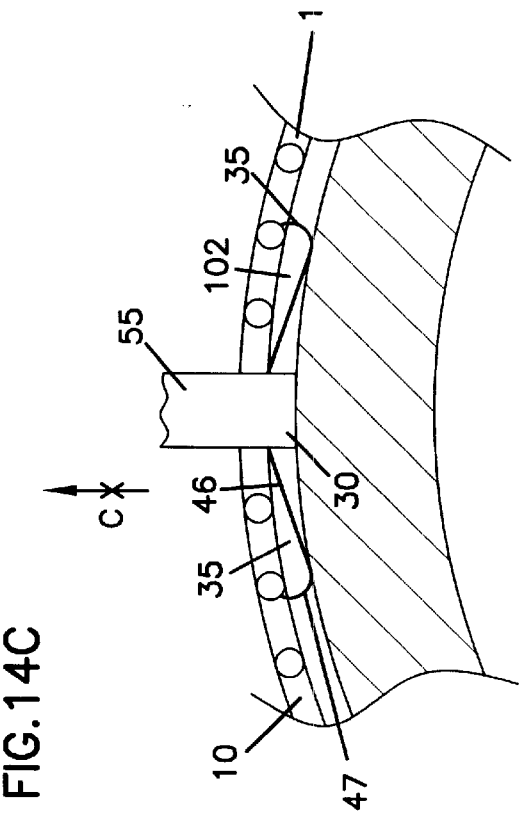
FIG. 14C is a cross sectional view of the placement apparatus of FIG. 14B.
Figure 14B:
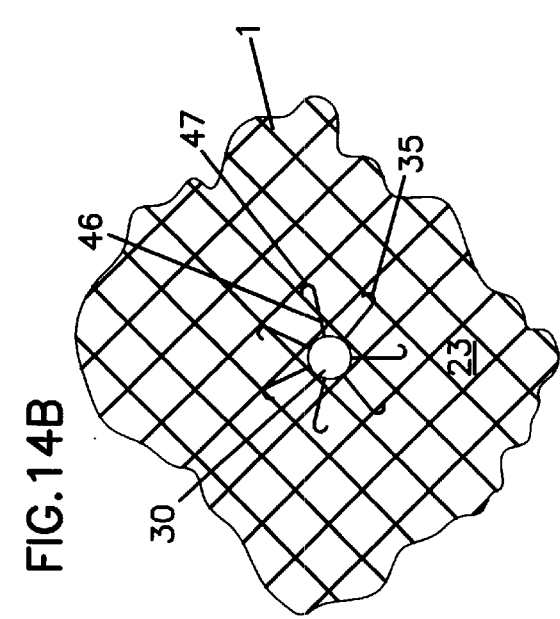
FIG. 14B is a top view of the placement apparatus of FIG. 14A.
Figure 14A:
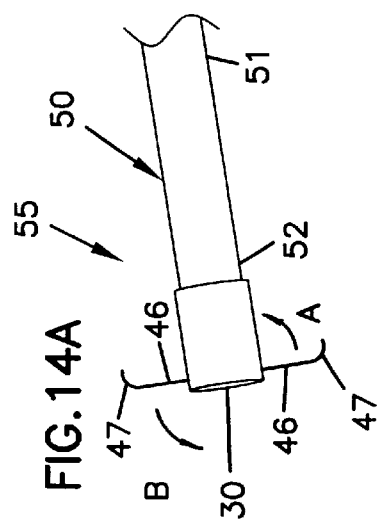
FIG. 14A is a side view of a placement apparatus according to the invention.

In other embodiments, the placement apparatus 102 is initially secured to the lead 55. In one such embodiment, the placement apparatus 102 may include at least one projection 35, such as a tine or hook, secured to the lead 55 (similar to commercially available lead attachments for embedding a lead into the myocardium). The projection 35 generally has a proximate end 46, secured to the lead 55, and a distal end 47. Preferably the projection(s) 35 is configured such that the distal end 47 is easily collapsed towards the proximate end 51 of the lead 55 (i.e., in the direction of arrow "A") but not in the opposite direction (i.e., in the direction of arrow "B"). Preferably, the placement apparatus 102 includes a plurality of projections 35 biased to extend radially outward from the lead 55 (See FIGS. 14A–C). To secure the lead 55 to the cardiac reinforcement device 1, the projections 35 of the placement apparatus 102 are urged radially inward (in the direction of arrow "A"), until they are approximately parallel with the lead 55. The lead 55 is then passed through an open cell 23 of the cardiac reinforcement device 1. Once the lead 55 extends through the open cell 23, the projections 35 are allowed to relax, and to again extend radially outward. The projections 35 thus secure the lead 55 to the cardiac reinforcement device 1 by grasping the fibers 20 of the cardiac reinforcement device 1.

Preferably, the projections 35 are constructed from a non-conductive material that is rigid enough such that lead 55 cannot be pulled out (in the direction of arrow "C") through the open cell 23 of the material. Suitable materials may include, but are not limited to, polyester, polyurethane, polypropylene, PTFE, or other polymeric material.

Figure 15A:
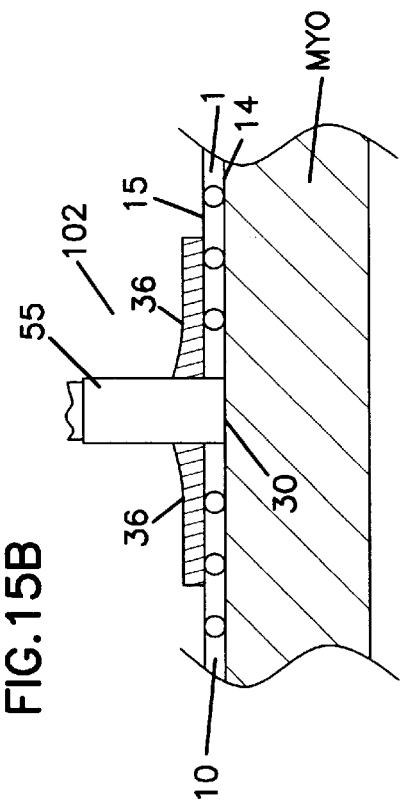
FIGS. 15A and 15B are a cross sectional views of a placement apparatus according to the invention.

In an alternate embodiment, the placement apparatus 102 is constructed as a flange 36 that biased to extend radially outward from the lead 55 (FIGS. 15A and B). Preferably, as with the projections 35 described above, the flange 36 is preferentially collapsible towards the proximate end of the lead 55. Thus, the flange 36 can be urged radially inward such that the lead 55 can be passed through an open cell 23 of the cardiac reinforcement device 1. The flange 36 is then allowed to relax and again extend radially outward to retain the lead 55 within the cardiac reinforcement device 1. As with the projections 35 described above, the flange 36 is preferably constructed using a nonconductive material that is rigid enough such that lead 55 cannot be pulled out (in the direction of arrow "C") through the open cell 23 of the material. Suitable materials may include, but are not limited to, polyester, polyurethane, polypropylene, PTFE, or other polymeric material.

Figure 15B:
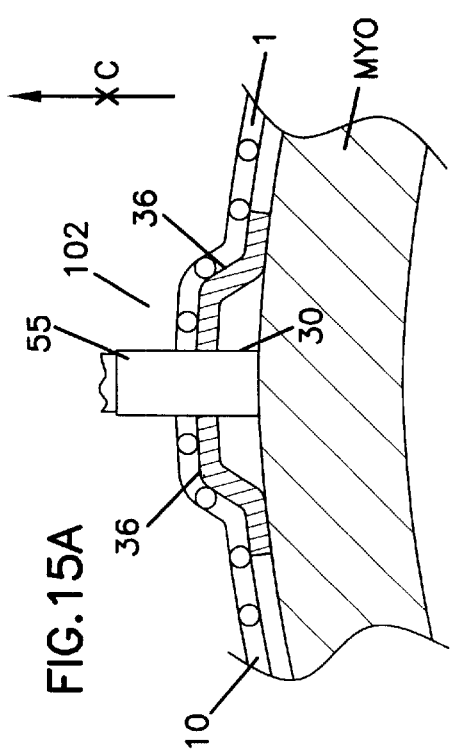

Alternately, the flange 36 may be secured to an interior 14 or exterior 15 surface of a cardiac reinforcement device 1 with sutures (FIG. 15B). For example, the flange 36 may be constructed from the materials described above and define multiple apertures for suturing the flange 36 to the cardiac reinforcement device. Alternately, the flange 36 may be constructed, at least in part, from a fabric (woven or mesh) that is capable of being sutured to the cardiac reinforcement device 1. If desired, the flange 36 can be sutured to the cardiac reinforcement device 1 either before or after the cardiac reinforcement device 1 is implanted.

Figure 16:
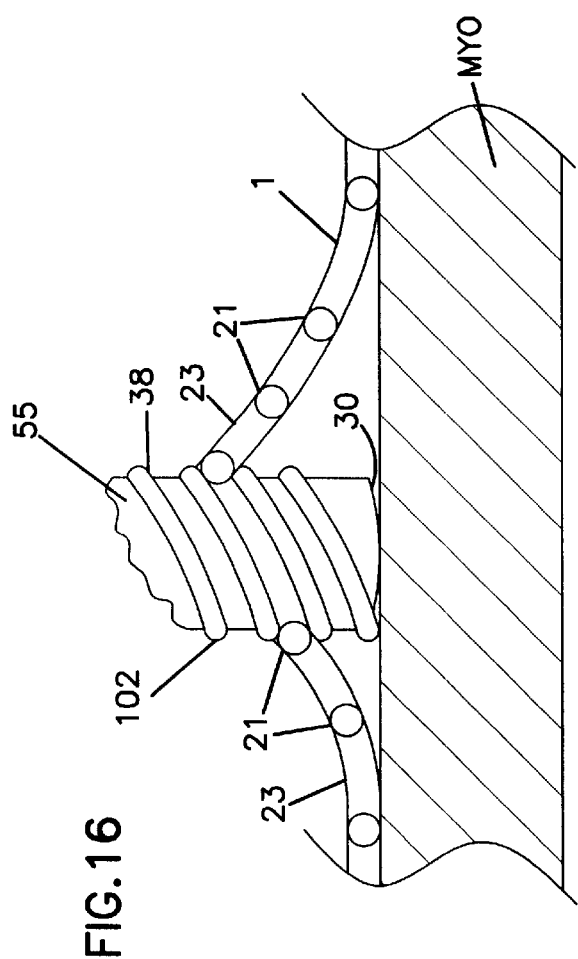
FIG. 16 is a cross sectional view of a placement apparatus according to the invention.

In yet another embodiment, the placement apparatus 102 includes threads 38 coiled along the distal end 52 of the lead 55 (FIG. 16). According to this embodiment, the lead 55 is secured to the cardiac reinforcement device by turning the lead 55 as it is urged through an open cell 23 of the cardiac reinforcement device 1. The fibers 21 of the cardiac reinforcement device 1 engage the threads 38 of the lead 55 to secure the lead 55 to the cardiac reinforcement device 1.

With the foregoing, a device and method have been taught to treat cardiac disease. The jacket 10 constrains further undesirable circumferential enlargement of the heart while not impeding other motion of the heart H. With the benefits of the present teachings, numerous modifications are possible. For example, the various placement apparatuses described herein may be combined in a single device. One combination might include threads 55 coiled around the distal end 52 of the lead that are configured to engage an interior surface of a pad 34. Other combinations can be readily envisioned.

What is claimed is:

1. A device for treating cardiac disease of a heart, the device comprising:
   biocompatible material configured to be secured to an epicardial surface of a heart;
   an electrotherapy instrument comprising at least one lead; and
   a placement apparatus configured to be secured to said biocompatible material, wherein said placement apparatus is capable of releasably securing a lead of said electrotherapy instrument to said biocompatible material.

2. A device according to claim 1, wherein the biocompatible material comprises a patch.

3. A device according to claim 1, wherein the biocompatible material comprises a jacket of flexible material adapted to be secured to said heart with said jacket having portions disposed on opposite sides of the heart, wherein said jacket is adapted to be adjusted on said heart to snugly conform to an external geometry of said heart and assume a maximum adjusted volume to constrain circumferential expansion of said heart beyond said maximum adjusted volume during diastole and permit substantially unimpeded contraction of said heart during systole.

4. A device according to claim 1, wherein said electrotherapy instrument comprises a cardiac pacing device.

5. A device according to claim 1, wherein said electrotherapy instrument comprises a defilbrillating device.

6. A device according to claim 1, wherein said electrotherapy instrument comprises more than one lead and said device comprises more than one placement apparatus.

7. A device according to claim 1, wherein said lead comprises at least one electrode and said placement apparatus is configured to position said electrode in electrical contact with said heart.

8. A device according to claim 7, wherein said placement apparatus is configured to position said electrode in electrical contact with a myocardium of said heart.

9. A device according to claim 1, wherein said placement apparatus is initially secured to said biocompatible material.

10. A device according to claim 9, wherein said placement apparatus comprises a snap comprising a base and a cap, each of which define an opening capable of housing a lead.

11. A device according to claim 10, wherein said base comprises an engagement member configured to operably engage an engagement member of said cap to secure said base to said cap.

12. A device according to claim 9, wherein said placement apparatus comprises a non-conductive pad, said pad defining an opening capable of housing a lead.

13. A device according to claim 12, wherein said biocompatible material is embedded within said pad.

14. A device according to claim 12, wherein sutures secure said pad to said biocompatible material.

15. A device according to claim 1, wherein said placement apparatus is initially secured to said lead.

16. A device according to claim 15, wherein said placement apparatus comprises at least one projection secured to said lead.

17. A device according to claim 16, wherein said placement apparatus comprises a plurality of projections extending radially outward from said lead.

18. A device according to claim 15, wherein said placement apparatus comprises a flange extending radially outward from said lead.

19. A device according to claim 18, wherein said flange is located proximate an interior surface of said biocompatible material when in use.

20. A device according to claim 19, wherein said flange is secured to the interior surface of said biocompatible material.

21. A device according to claim 20, wherein sutures secure said flange to the interior surface of said biocompatible material.

22. A device according to claim 18, wherein said flange is secured to an exterior surface of said biocompatible material.

23. A device according to claim 22, wherein said flange is sutured to an exterior surface of said biocompatible material.

24. A device according to claim 15, wherein said placement apparatus comprises threads coiled along a distal end of said lead, said threads configured to engage fibers of an open cell of said biocompatible material to secure said lead to said biocompatible material.

25. A method for treating cardiac disease of a heart, said method comprising:
(a) surgically accessing said heart;
(b) securing a biocompatible material to said heart; and
(c) determining a desired location for at least one lead of an electrotherapy instrument, said step of determining comprising:
  (i) releasably securing said at least one lead to said biocompatible material;
  (ii) transmitting an electrical impulse to said heart from said at least one lead; and
  (iii) monitoring cardiac response to said electrical impulse;
(d) securing said lead to said biocompatible material at said desired location; and
(e) surgically closing access to said heart while leaving the device in place.

26. The method according to claim 25, wherein said biocompatible material comprises a patch.

27. The method according to claim 25, wherein said step of securing said lead to said biocompatible material at said desired location comprises securing said lead to a location on a left ventricular free wall of said heart.

28. The method according to claim 25, wherein said lead comprises at least one placement apparatus.

29. The method according to claim 25, wherein said biocompatible material comprises a jacket that defines a volume between an open upper end and a lower end, said jacket dimensioned for an apex of said heart to be inserted into said volume through said open upper end.

30. The method according to claim 29, further comprising adjusting said jacket on said heart to snugly conform to an external geometry of said heart and assume a maximum adjusted volume for said jacket to constrain circumferential expansion of said heart beyond said maximum adjusted volume during diastole and permitting unimpeded contraction of said heart during systole.

31. The method according to claim 25, wherein said step of releasably securing said at least one lead to said biocompatible material comprises suturing said at least one lead to said biocompatible material.

32. The method according to claim 31, wherein said step of securing said lead to said biocompatible material at said desired location comprises gluing said lead to said biocompatible material with a bioglue.

33. The method according to claim 25, wherein said biocompatible material comprises at least one placement apparatus.

34. The method according to claim 33, wherein said biocompatible material comprises a plurality of placement apparatuses.

35. The method according to claim 33, wherein said step of releasably securing said at least one lead to said biocompatible material comprises releasably securing said at least one lead to said at least one placement apparatus.

36. The method according to claim 25, wherein said electrotherapy instrument comprises multiple leads.

37. The method according to claim 36, further comprising a step of transmitting an electrical impulse from at least one lead to said heart after said step of surgically closing access to said heart.

38. The method according to claim 37, comprising simultaneously transmitting an electrical impulse from said multiple leads.

39. The method according to claim 37, comprising sequentially transmitting an electrical impulse from said multiple leads.

40. The method according to claim 37, wherein said step of transmitting an electrical impulse comprises cardiac pacing therapy.

41. The method according to claim 37, wherein said step of transmitting an electrical impulse comprises defibrillation therapy.

* * * * *

UNITED STATES PATENT AND TRADEMARK OFFICE
CERTIFICATE OF CORRECTION

PATENT NO.    : 6,564,094 B2
DATED         : May 13, 2003
INVENTOR(S)   : Alferness et al.

It is certified that error appears in the above-identified patent and that said Letters Patent is hereby corrected as shown below:

Title page,
Item [56], References Cited, OTHER PUBLICATIONS, "Capomolla, S. et al." reference, after "ventricular function", please add -- *American Heart Journal*, vol. 134, pp. 1089-1098 (Dec. 1997). --
U.S. PATENT DOCUMENTS, delete "*American Heart Journal*, vol. 134, pp. 1089-1098 (Dec. 1997)." after 600/37 for the "6,432,039 B1" reference.

Column 9,
Line 63, "polyletrafluoroethylene" should read -- polytetrafluoroethylene --

Column 13,
Line 20, "device I would" should read -- device 1 would --

Column 17,
Line 4, "defilbrillating" should read -- defibrillating --

Signed and Sealed this

Twenty-third Day of September, 2003

JAMES E. ROGAN
*Director of the United States Patent and Trademark Office*